(12) United States Patent
Spiegelman et al.

(10) Patent No.: US 11,154,792 B2
(45) Date of Patent: Oct. 26, 2021

(54) METHODS AND SYSTEMS FOR GENERATING PROCESS GASES

(71) Applicant: RASIRC, INC., San Diego, CA (US)

(72) Inventors: Jeffrey Spiegelman, San Diego, CA (US); Douglas Shepherd, El Cajon, CA (US); Russell J. Holmes, San Diego, CA (US); Zohreh Shamsi, San Diego, CA (US)

(73) Assignee: RASIRC, INC., San Diego, CA (US)

( * ) Notice: Subject to any disclaimer, the term of this patent is extended or adjusted under 35 U.S.C. 154(b) by 458 days.

(21) Appl. No.: 15/751,044

(22) PCT Filed: Aug. 10, 2016

(86) PCT No.: PCT/US2016/046334
§ 371 (c)(1),
(2) Date: Feb. 7, 2018

(87) PCT Pub. No.: WO2017/027581
PCT Pub. Date: Feb. 16, 2017

(65) Prior Publication Data
US 2018/0229149 A1    Aug. 16, 2018

Related U.S. Application Data

(60) Provisional application No. 62/203,197, filed on Aug. 10, 2015.

(51) Int. Cl.
*B01B 1/00* (2006.01)
*C23C 16/448* (2006.01)
(Continued)

(52) U.S. Cl.
CPC .............. *B01B 1/005* (2013.01); *A61L 2/20* (2013.01); *A61L 2/208* (2013.01); *A61L 2/26* (2013.01);
(Continued)

(58) Field of Classification Search
CPC . A61L 2202/14; B01B 1/005; C23C 16/4481; G03F 7/423
See application file for complete search history.

(56) References Cited

U.S. PATENT DOCUMENTS 2,958,391 A    11/1960    Rosset
2002/0178797 A1    12/2002    Pawliszyn
(Continued)

FOREIGN PATENT DOCUMENTS

JP    2015514005 A    5/2015
WO    WO-2013148262 A1 *    10/2013    ............... B01F 3/02

OTHER PUBLICATIONS

PCT/US2016/046334 International Search Report dated Dec. 20, 2016.
(Continued)

*Primary Examiner* — Justin C Dodson
*Assistant Examiner* — Dilnessa B Belay
(74) *Attorney, Agent, or Firm* — MLO, a professional corp.

(57) ABSTRACT

Methods for the gas-phase delivery of gases, such as process gases, from the gas phase of a multicomponent source liquid are provided. The methods are generally directed to the generation of process gases having mass flow rates which are proportional to the input power delivered to the multi-component source liquid containers. The methods may be used to deliver process gases to critical process applications.

33 Claims, 10 Drawing Sheets

(51) Int. Cl.
    *A61L 2/20*     (2006.01)
    *A61L 2/26*     (2006.01)
    *F22B 3/02*     (2006.01)
    *H05B 1/02*     (2006.01)
    *G03F 1/82*     (2012.01)
    *G03F 7/42*     (2006.01)
    *H01L 21/02*     (2006.01)

(52) U.S. Cl.
    CPC ...... *C23C 16/4481* (2013.01); *C23C 16/4485* (2013.01); *F22B 3/02* (2013.01); *H05B 1/0297* (2013.01); *A61L 2202/14* (2013.01); *G03F 1/82* (2013.01); *G03F 7/423* (2013.01); *H01L 21/02057* (2013.01); *H01L 21/02271* (2013.01)

(56) References Cited

U.S. PATENT DOCUMENTS

| | | | |
|---|---|---|---|
| 2003/0059340 A1* | 3/2003 | Chien | A61L 2/208 422/30 |
| 2011/0272354 A1 | 11/2011 | Mitra et al. | |
| 2012/0298207 A1* | 11/2012 | Woelk | C23C 16/4481 137/2 |
| 2013/0233170 A1* | 9/2013 | Spiegelman | B01D 69/141 95/23 |
| 2015/0068611 A1 | 3/2015 | Alvarez, Jr. et al. | |

OTHER PUBLICATIONS

Office Action dated Oct. 6, 2020 for Japanese Patent Application No. 2018-506896.

* cited by examiner

METHODS AND SYSTEMS FOR GENERATING PROCESS GASES

CROSS-REFERENCE TO RELATED APPLICATIONS

This application is a 371 of PCT/US16/46334 filed on Aug. 10, 2016, which claims priority to U.S. Provisional Application No. 62/203,197, the entire contents of which are incorporated herein by reference.

TECHNICAL FIELD

A method, systems, and devices for the vapor phase delivery of high purity process gases are provided. Particularly, the method, systems, and devices are for low volatility process gases obtained from a source liquid. The method, systems, and devices are typically used in the field of manufacturing micro-electronics and other critical process applications.

BACKGROUND

Process gases are used in the manufacturing and processing of micro-electronics, among other applications. They are used in applications in which process control and purity are critical considerations. Process gases and carrier gases are also used to deliver a chemical to specific locations in a product, when the dimensions of the product are too small for a liquid to reach. As the dimensions of microelectronic elements continue to shrink, as is the trend in the industry, manufacturing these products requires delivery of chemicals into spaces measured in nanometers, or even picometers. At this small scale, the surface tension of liquids limits their ability to reach deep channels or small spaces. Gaseous forms of the chemicals do not face this limitation by surface tension. For this reason, gas is the form of matter best suited to these types of applications.

Examples of applications in which process gases are used include: microelectronics applications, wafer cleaning, wafer bonding, photolithography mask cleaning, atomic layer deposition, chemical vapor deposition, flat panel displays, disinfection of surfaces contaminated with bacteria, viruses, DNA, RNA and other biological agents, industrial parts cleaning, pharmaceutical manufacturing, and the production of nanomaterials, power generation and control devices, fuel cells, and power transmission devices.

In order to deliver specific amounts of gas from a source liquid, it is necessary to tightly control the temperature, pressure, and flow rate of the carrier gas. Further, process gases are used in applications in which a low mass flow of process chemicals is useful. A greater degree of accuracy and cleanliness is possible with gas delivery than is possible with liquid delivery. For this reason, process gases are preferable from a standpoint of ease of delivery, accuracy, and purity. The currently available delivery devices and methods of process and carrier gases are insufficient for ensuring consistent, precise, and safe delivery of controlled quantities of process gases and carrier gases obtained from a source liquid in many microelectronics applications and other critical processes.

The devices previously used for precise delivery of process chemicals in microelectronics applications include bubblers and vaporizers, both of which have many significant barriers to consistent, precise, and safe delivery of process chemicals. Bubblers are not compatible or effective with new chemistries, and they rely on direct liquid to carrier gas mass transfer by bubbling carrier gas through the source liquid. Bubblers typically cause problems with excessive micro-droplet formation of the process chemical, particle generation, and failure to fully saturate the carrier gas. These problems interfere with the precise and consistent delivery of chemicals. Additional barriers to implementation of bubblers in industrial applications are the necessarily tight control of temperature of the liquid, the system pressure, and the carrier gas flow rate. There are significant difficulty in ensuring the stability of each of these three measurements, and in calibration and maintenance of them.

Vaporizers, similar to bubblers, also have the problem of generating small micro-droplets of the output chemical, disrupting the smooth output of gaseous chemical that is required for the application. Additionally, vaporizers require high temperatures for vaporization of the liquid chemical. These high temperatures can lead to a decomposition of the liquid molecule, which alters the stability and concentration of the output product. Vaporizers are not as accurate or clean as the herein described methods and devices.

Significant issues arise with existing methods when using low vapor pressure liquids as process chemicals. Examples of low vapor pressure liquids often used as process chemicals include water, inorganic acids, organic acids, inorganic bases, organic bases, and inorganic and organic solvents. A particular process gas of interest is hydrogen peroxide gas and others include hydrazine, alcohols and amines. Liquid dispensation is more difficult to precisely control than gas. However, these chemicals are generally not available in the gas phase, and must be converted to gas in situ. The typical practice is to vaporize the process chemical component at or near the point of use. This process leaves nonvolatile contaminants behind, purifying the process chemical. Additionally, an approximately 1000-fold increase in volume occurs when a chemical is converted from liquid to gas. Microelectronics applications and other critical processes typically have extensive gas handling systems that make gaseous delivery considerably easier than liquid delivery.

During gas phase delivery of low volatility compounds, such as hydrogen peroxide or other similar gases such as hydrazine, existing methods and technology create several problems. When using a single component source liquid, the high number of variables in the equation prevents reliable and replicable calibration of the system. The system must be calibrated for a wide range of pressures of the carrier gas, which is difficult and time-consuming. Additionally, the system must be calibrated for the temperature of the source liquid, which often has a widely variable thermal profile at different locations within the liquid and therefore cannot be accurately calibrated. Finally, the flow rate of the carrier gas must also be taken into account. The resulting calibration equation is highly non-linear, and therefore difficult to calibrate with.

To mitigate the problems that arise with low volatility compounds, one method commonly used is to utilize a multi-component solution as the source liquid, wherein the process chemical is mixed with a more volatile solvent, such as water or an organic solvent (e.g., isopropanol). This is particularly suitable for aqueous hydrogen peroxide or hydrazine solutions, as high concentrations of hydrogen peroxide or hydrazine present an explosion hazard. However, when a multi-component solution is the source liquid to be delivered (e.g., hydrogen peroxide and water), Raoult's Law for multi-component solutions becomes relevant. According to Raoult's Law, for an idealized two-component solution, the vapor pressure of the solution is equal to the weighted sum of the vapor pressures for a pure solution of each component, where the weights are the mole fractions of each component:

$$P_{tot}=P_aX_a+P_bX_b$$

In the above equation, $P_{tot}$ is the total vapor pressure of the two-component solution, $P_a$ is the vapor pressure of a pure solution of component A, $X_a$ is the mole fraction of component A in the two-component solution, $P_b$ is the vapor pressure of a pure solution of component B, and $X_b$ is the mole fraction of component B in the two-component solution. Therefore, the relative mole fraction of each component is different in the liquid phase than it is in the vapor phase above the liquid. Specifically, the more volatile component (i.e., the component with the higher vapor pressure) has a higher relative mole fraction in the gas phase than it has in the liquid phase. In addition, because the gas phase of a typical gas delivery device, such as a bubbler, is continuously being swept away by a carrier gas, the composition of the two-component liquid solution, and hence the gaseous head space above the liquid, is dynamic. Unless the more volatile component is continuously replenished, the mole fraction of the less volatile component will increase in the liquid over time.

Thus, according to Raoult's Law, if a vacuum is pulled on the head space of a multi-component liquid solution or if a traditional bubbler is used to deliver the solution in the gas phase, the more volatile component of the liquid solution will be preferentially removed from the solution as compared to the less volatile component. This limits the concentration of the less volatile component that can be delivered in the gas phase. For instance, if a carrier gas is bubbled through a 30% hydrogen peroxide/water solution, only about 295 ppm of hydrogen peroxide will be delivered, the remainder being all water vapor (about 20,000 ppm) and the carrier gas. See USP Technologies, Vapor Pressures of $H_2O_2$, http://www.h2o2.com/technical-library/physical-chemical-properties/physical-properties/defaultaspx?pid=25.

The outcome of using a multi-component solution is a differential delivery rate, which prevents a repeatable process control. Process recipes cannot be written around continuously changing mixtures. Controls for measuring a continuously changing ratio of the components of the source liquid are not readily available. If they are available, they are costly and difficult to integrate into the process. Furthermore, certain solutions become hazardous if the relative ratio of the components of the source liquid changes. For example, hydrogen peroxide in water may become explosive at concentrations over about 75%. Delivering hydrogen peroxide by bubbling a dry gas through an aqueous hydrogen peroxide solution, or evacuating the head space above such a solution, can take a safe solution (e.g., 30% $H_2O_2/H_2O$) and convert it to a hazardous material (e.g., >75% $H_2O_2/H_2O$) because the more volatile component, $H_2O$, is preferentially removed over time.

Multi-component solutions also present the same difficulties of single-component solutions of source chemicals, including the difficulties of calibrating using a non-linear equation which involves calculating shifting values for source liquid temperature, carrier gas flow rate, and carrier gas vapor pressure.

Calibration of precise delivery equipment presents many difficulties. Mass pickup, which must be monitored to ensure consistent delivery of process chemical, is a function of the vapor pressure of the source liquid, and the pressure and flow rate of carrier gas. The vapor pressure curve for liquids is highly non-linear. The application systems in question usually work at higher temperatures and at high vapor pressures. In this range, small changes in temperature significantly change the mass of vapor generated. In the most useful and commonly used temperature range, sensitivity and accuracy are poor.

Typically mass pickup rate is controlled by calibrating with the temperature of the source liquid and the mass flow rate of the carrier gas. However, the thermal profile of the source liquid is dynamic and not uniform, reducing the accuracy of calibrating by this measurement. Additionally, when changing the temperature or flow rate of the system, which is done any time the system is initially engaged, or for any other number of reasons, there is a significant time delay before the temperature of the liquid is stabilized and calibration becomes possible. Any further addition of source liquid during the process disturbs the thermal profile of the source liquid.

The methods, systems, and devices disclosed herein address a problem of controlling the mass pickup of vaporized gas from a source liquid in precise chemical delivery systems. Mass pickup is a function of the vapor pressure of the source liquid and the pressure and flow rate of the carrier gas. Before, the mass pickup was controlled via calibrating the pickup of vapor by monitoring the temperature of source liquid and the mass flow rate of the carrier gas. There are several problems that arise with this prior method. Because the calibration is dependent on the full saturation of the carrier gas, the correct flow rate of the carrier gas is difficult to control. It is also difficult to control the liquid temperature. This is due to the large amount of liquid, and the dynamic thermal profile of the liquid, which leaves uncertainty about the temperature of the liquid at the specific location of vaporization. Because of the dynamic nature of the thermal profile of the liquid, it is difficult to optimize a specific placement for the thermal couple. The system has to be calibrated for a range of carrier gas flow rates and vaporizer temperatures. Because the heater is not in direct contact with the liquid, there is a time delay between transitioning the flow rate or temperature and the stabilization of the temperature.

Because the vapor pressure curve is highly non-linear, any change in partial pressure affects the amount of mass picked up by the carrier gas. Systems are usually operated at higher temperatures for higher vapor pressures, at which range the sensitivity and accuracy are poor. Any change in the location of the temperature sensor or in the thermal liquid profile dramatically affects the accuracy of the mass of vapor generated. The mass flow is also dependent on the carrier gas pressure at the gas vapor interface, as well as the relationship between the height of the vaporizer and the carrier gas flow rate.

In order to conserve and minimize risk by using expensive or dangerous liquids as seldom as possible, it is desirable to use water as a surrogate liquid for more dangerous or expensive liquids when calibrating and/or testing a vaporizer. However, due to the multiple elements of the calibration equation, this is a difficult task using existing methods. There are too many variables to translate between the intended process liquid and water for water to be accurately and easily used. In order to facilitate this surrogate calibration and testing, one would need a control and calibration method independent of the flow rate of the carrier gas, independent of the temperature of the liquid, and independent of the pressure of the carrier gas.

The proposed method claimed herein is to control only the power input into the source liquid. The power required to vaporize liquid is generally much greater than the power required to raise the temperature of a liquid or a gas. The amount of vapor generated is directly and somewhat linearly related to the amount of power input into a system. This method allows for easier calibration, because instead of controlling and calibrating for the flow rate and pressure of the carrier gas and the temperature of the liquid, the only measurement that needs to be controlled is the amount of power input into the liquid. Because the values of heat of vaporization for most chemistry are already known, a surrogate chemical such as water may be used for the calibration of a system. Even very complicated blends of chemistries need only be compared with simple two-point calibration curves in order to determine the surrogate coefficient. This enhanced possibility of using safe and inexpensive chemicals as calibration surrogates improves productivity, safety, and conserves resources.

SUMMARY OF CERTAIN EMBODIMENTS

There are many applications in which the disclosed methods and devices will be useful. One example of an embodiment of the methods, systems and devices disclosed herein is in the manufacturing of semiconductors where critical dimensions are <10 nanometers, where liquid processing is not always effective. The surface tension of liquids prevents the liquid chemicals from accessing the bottoms of vias or trenches in high aspect ratio device structures. The methods, systems and devices disclosed herein may also be applied in other microelectronics applications and other critical processes, for safe and controlled transfer and purification of low volatility compounds from multi-component liquid solutions into a gas.

The methods, systems and devices disclosed herein may also be used for decontamination. Materials contaminated with pathogenic microorganisms can present a large problem in particular environments, including in medical, industrial, and laboratory settings. Currently used methods for decontamination face limitations in their effectiveness Processes involving in vitro nucleic acids amplification techniques can generate false outcomes when stray nucleic acids contaminate the process. Bleach is often used for decontamination, but it is corrosive to metal, which presents a long term maintenance problem. Ultraviolet light can be used to decontaminate, but this method cannot kill pathogens that are not incident to the rays of UV light, so again this method is unsuitable for very small passages or crevices within devices to be decontaminated. High power plasma is not suitable or appropriate for delicate machinery with sensitive electronics and can generally only be applied in vacuum.

Using hydrogen peroxide gas, or $H_2O_2$ gas, as a decontaminant, is a desirable method. Its decomposition products, $O_2$ and $H_2O$, are not toxic and not harmful to the environment. Additionally, $H_2O_2$ gas can reach places that liquids cannot, making it an ideal material for decontamination purposes.

In one aspect, a method is provided for generating a process gas stream comprising applying an input power to a container comprising a multi-component source liquid having a gas phase wherein the multi-component source liquid comprises a first component and a second component which is less volatile than the first component and generating a gas stream comprising the less volatile component at a stable steady-state mass flow rate, wherein the container is in thermal contact with the multi-component source liquid.

In another aspect, a method of generating a gas stream comprising (a) applying a first specified power to a container comprising a multi-component source liquid wherein the multi-component source liquid comprises a first component and a second component which is less volatile than the first component; (b) measuring the resulting mass flow of the less volatile component in the gas phase resulting from the from the application of the first specified power to the container; (c) changing the power to a second specified power to the container; (d) measuring the resulting mass flow of the less volatile component in the gas phase resulting from the application of the second specified power to the container; (e) applying an input power to the container wherein the power applied is determined by (i) determining the linear function that describes applied power as a function of mass flow rate from steps (a)-(d) and (ii) applying the input power at a level corresponding to a particular mass flow rate from the linear function; and (f) generating a process gas stream comprising the less volatile component at a stable steady-state mass flow rate, wherein the container is in thermal contact with the multi-component source liquid is provided.

In another aspect, devices and systems are disclosed that employ the methods of generating a gas stream and controlling the precise delivery of a process chemical, e.g., $H_2O_2$, to a microelectronics application or other critical processes, e.g., semiconductor manufacturing or decontamination.

DETAILED DESCRIPTION OF CERTAIN EMBODIMENTS

Figure 1:
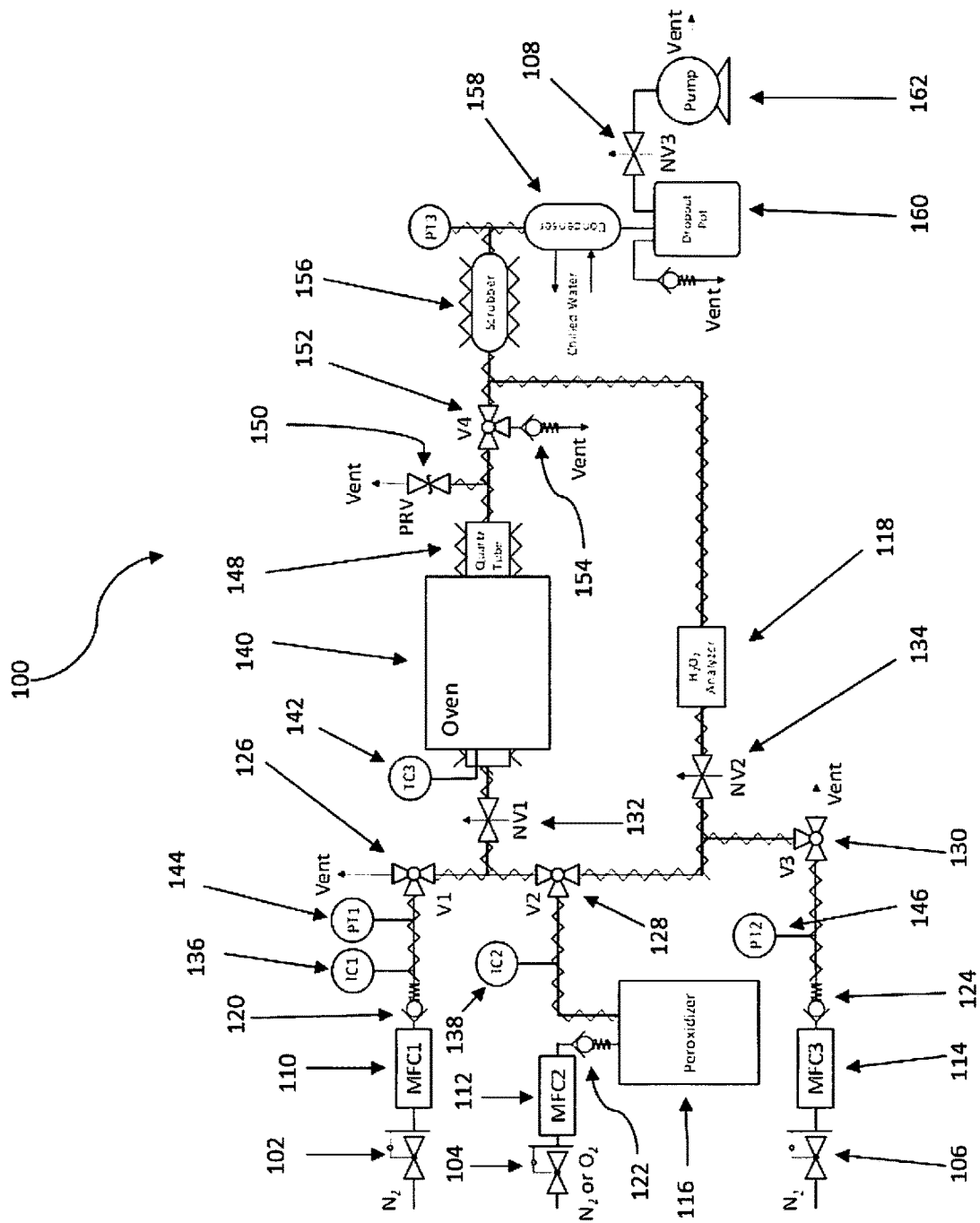
FIG. 1. is a schematic view of the apparatus constructed to determine if the Peroxidizer's power equation provides stable output under vacuum conditions.

In the methods disclosed herein, the power input into the source liquid is controlled so as to deliver a process gas. The power required to vaporize liquid is generally much greater than the power required to raise the temperature of a liquid or a gas. In the methods disclosed herein, the amount of vapor generated is directly and linearly related to the amount of power input into a system. This method allows for easier calibration, because instead of controlling and calibrating for the flow rate and pressure of the carrier gas and the temperature of the liquid, the only measurement that needs to be controlled is the amount of power input into the liquid.

There are many critical process applications in which the methods, systems, and devices disclosed herein may be used. One example is in the manufacturing of semiconductors where critical dimensions are <10 nanometers, and where liquid processing is not always effective. The surface tension of liquids prevents the liquid chemicals from accessing the bottoms of vias or trenches in high aspect ratio device structures. The methods, systems, and devices disclosed herein may also be applied in microelectronics, for safe and controlled transfer and purification of low volatility compounds from multi-component liquid solutions into a gas.

The methods, systems, and devices disclosed herein may also be used for decontamination. Materials contaminated with pathogenic microorganisms can present a large problem in particular environments, including in medical, industrial, and laboratory settings. Currently used methods for decontamination face limitations in their effectiveness Processes involving in vitro nucleic acids amplification techniques can generate false outcomes when stray nucleic acids contaminate the process. Bleach is often used for decontamination, but it is corrosive to metal, which presents a long term maintenance problem. Ultraviolet light can be used to decontaminate, but this method cannot kill pathogens that are not incident to the rays of UV light, so again this method is unsuitable for very small passages or crevices within devices to be decontaminated. High power plasma is not suitable or appropriate for delicate machinery with sensitive electronics and can generally only be applied in vacuum.

Using hydrogen peroxide gas, or $H_2O_2$ gas, as a decontaminant, is a desirable method. Its decomposition products, $O_2$ and $H_2O$, are not toxic and not harmful to the environment. Additionally, $H_2O_2$ gas can reach places that liquids cannot, making it useful for decontamination applications.

DEFINITIONS

The term "substantially gas-impermeable membrane" as used herein is a broad term, and is to be given its ordinary and customary meaning to a person of ordinary skill in the art (and is not to be limited to a special or customized meaning), and refers without limitation to a membrane that is relatively permeable to other components that may be present in a gaseous or liquid phase, e.g., water or hydrogen peroxide, but relatively impermeable to other gases such as, but not limited to, hydrogen, nitrogen, oxygen, carbon monoxide, carbon dioxide, clean dry air, room air, hydrogen sulfide, hydrocarbons (e.g., ethylene), volatile acids and bases, refractory compounds, and volatile organic compounds. Examples of substantially gas-impermeable membranes include NAFION® and salt derivatives as well as AQUIVON® or 3M IONOMER®. Such membranes include additional membranes known in the art.

The term "ion-exchange membrane" as used herein is a broad term, and is to be given its ordinary and customary meaning to a person of ordinary skill in the art (and is not to be limited to a special or customized meaning), and refers without limitation to a membrane comprising chemical groups capable of combining with ions or exchanging with ions between the membrane and an external substance. Such chemical groups include, but are not limited to, sulfonic acid, carboxylic acid, phosphoric acid, phosphinic acid, sulfamides, sulfonyl imides, arsenic groups, selenic groups, phenol groups, and salts thereof. When making modifications to ion-exchange membranes resulting in salts, such salts are referred to herein as "ion-exchange membrane salts."

The term "critical process application" as used herein is a broad term, and is to be given its ordinary and customary meaning to a person of ordinary skill in the art (and is not to be limited to a special or customized meaning), and refers without limitation to a process or application in which process control and purity are critical considerations. Examples of critical processes and applications include without limitation microelectronics applications, wafer cleaning, wafer bonding, photoresist stripping, silicon oxidation, surface passivation, photolithography mask cleaning, atomic layer deposition, chemical vapor deposition, flat panel displays, disinfection of surfaces contaminated with bacteria, viruses and other biological agents, industrial parts cleaning, pharmaceutical manufacturing, production of nano-materials, power generation and control devices, fuel cells, and power transmission devices.

The term "relatively constant" as used herein is a broad term, and is to be given its ordinary and customary meaning to a person of ordinary skill in the art (and is not to be limited to a special or customized meaning), and refers without limitation to a value that, although it may change with time, does not change so substantially so as to render the value inoperative or substantially less operative. In the context of increasing the concentration of a low volatile component, such as $H_2O_2$, it means maintaining a concentration at sufficiently high levels so as to provide a stable gas delivery of the low component gas for sufficient time to be applied to a critical process or application. For example, maintaining a standard deviation of to within 3% or up to 5% of the mean for an hour would be considered relatively constant.

The term "equilibrium concentration" as used herein means the maximum amount of the less volatile component that may be delivered into the gas phase to be used, e.g., to decontaminate a material, and will be dependent upon temperature and head space pressure. Under such equilibrium conditions, the molar ratio of the less volatile component to the higher volatile component in the gas phase will be equivalent to the molar ratio of the less volatile component to the higher volatile component in the solution phase of the liquid used to replenish the multi-component source liquid. In solutions with multiple components, under such equilibrium conditions in accordance with the present invention, the molar ratio of the less volatile component to the higher volatile components in the gas phase will be equivalent to the molar ratio of the less volatile component to the higher volatile components in the solution phase of the liquid used to replenish the multi-component source liquid.

The term "stable" in the context of the output gas comprising the less volatile component from the multi-component source liquid, such as hydrogen peroxide in the gas-phase at a stable stead-state concentration means an output concentration that does not vary beyond certain parameters such as, for example, by more than 10% in some embodiments and not by more than 5%, 3% or 2% in other embodiments. The term applies once an equilibrium concentration of the less volatile component in the gas phase has been achieved and is being delivered to a critical process or application. The percentages herein are the standard deviation from the mean with respect to the mean of measured gas output.

The term "stable steady-state concentration" in the context of the output gas comprising the less volatile component from the multi-component source liquid means an output that has increased to a concentration that is stable and in equilibrium as those terms are used herein.

The term "leak rate" as used herein is a broad term, and is to be given its ordinary and customary meaning to a person of ordinary skill in the art (and is not to be limited to a special or customized meaning), and refers without limitation to the mass or moles of a particular gas that penetrates the membrane surface area per unit of time.

The term "gas" means gaseous species that is not a liquid, solid or a plasma as those terms are well understood in the art. Further, a gas is not a mist or a fog as would be generated, for example, by a nebulizer or atomizer. As used herein, the term gas further means that there are fewer than 100 particles of liquid from the gas generation source liquid greater than 100 nm in size at standard temperature and pressure conditions in a volume of one liter as measured with a standard condensation nucleation counter. In certain critical application processes where particles from droplet are detrimental, the term gas may preferably means that there are less than 10 particles greater than 100 nm, 50 nm, 25 nm, or 10 nm at standard temperature and pressure conditions in a volume of one liter as measured with a standard condensation nucleation counter available from MSP in Minnesota, Particle Measuring Systems or other readily available commercial instruments. In a multicomponent liquid, such as water and hydrogen peroxide, when volatilized and delivered to a critical process application such as a material to be decontaminated, the hydrogen peroxide is in the gas phase. By comparison, it is possible that water, when volatilized and introduced into a carrier gas, may be either a gas or a vapor provided, however, that the output to the material to be decontaminated is a gas.

The term "process gas" as used herein is a broad term, and is to be given its ordinary and customary meaning to a person of ordinary skill in the art (and is not to be limited to a special or customized meaning), and refers without limitation to a gas that is used in a critical process application, such as the decontamination of a material or cleaning the surfaces of semiconductors or the chemical modification of semiconductor surfaces to form an oxide, hydroxyl ligand. Similarly, such surfaces may be passivated by the removal of carbon atoms, or reacted with photoresist or photoresist byproducts, or annealing spin-on dielectrics or spin-on silicon based precursors. Exemplary process gases are water, inorganic acids, organic acids, inorganic bases, organic bases, and inorganic and organic solvents. A particular process gas is hydrogen peroxide gas. Others include hydrazine, alcohols and amines.

The term "carrier gas" as used herein is a broad term, and is to be given its ordinary and customary meaning to a person of ordinary skill in the art (and is not to be limited to a special or customized meaning), and refers without limitation to a gas that is used to carry another gas through a process train, which is typically a train of piping. Exemplary carrier gases are nitrogen, argon, hydrogen, oxygen, $CO_2$, clean dry air, room air, helium, or other gases or combinations thereof that are stable at room temperature and atmospheric pressure. A carrier gas may be an inert gas. In some embodiments, the carrier gas is nitrogen. The carrier gas may be solely an inert gas or it may have one or more additional components. A carrier gas may further comprise water, for example. By "dry nitrogen" what is meant is a nitrogen gas substantially free of water. In other embodiments, the carrier gas may be hydrogen, clean dry air, oxygen, ozone, or combinations thereof. In some embodiments, the carrier gas may be substantially free of water. In certain embodiments, the carrier gas is not passed through a humidifier. In some embodiments, the carrier gas contains an inert gas and water. As used herein, when water is identified as a component of the gas, unless otherwise provided, it is understood to be water in the gas phase.

The term "substantially dry carrier gas" means gas, or a particular kind of gas if in relation to clean dry air or nitrogen for example, that is dehumidified by methods known in the art reduce moisture in a gas so as to deliver a gas that is as dry as practicable. Such methods include, but are not limited to using gas purifiers such as those available from commercial manufacturers.

The term "pre-loaded carrier gas" as used herein is a broad term, and is to be given its ordinary and customary meaning to a person of ordinary skill in the art (and is not to be limited to a special or customized meaning), and refers without limitation to a carrier gas containing an amount of one or more component(s) of a source liquid. In some embodiments, the pre-loaded carrier gas contains an inert gas and water. In another embodiment, the pre-loaded carrier gas comprises one or more of nitrogen, argon, hydrogen, oxygen, $CO_2$, clean dry air, helium, or other gases that are stable at room temperature and atmospheric pressure and water. A pre-loaded carrier gas is also considered a carrier gas.

The term "undersaturated" means, in the context of a gas, such as a carrier gas or carrier gas, that the partial pressure of the gas is less than the maximum partial pressure for that gas in the head space or the carrier gas or carrier gas for the given temperature and pressure. The term undersaturated applies at a point specific point in time. The carrier gas may be saturated for a specific temperature and pressure and later be modified by reducing the pressure or increasing the temperature such that the head space or carrier gas is now undersaturated.

The term "oversaturated" means, in the context of a gas, such as a carrier gas or carrier gas, that the that the partial pressure of the gas is greater than the maximum partial pressure for that gas in the head space or the carrier gas or carrier gas for the given temperature and pressure. In some embodiments of methods, systems, and devices disclosed herein, the gas stream delivered to the critical process application is at a higher partial pressure of the component less volatile than water than the partial pressure of that component from the multi-component source liquid used to replenish prior to delivery of that liquid.

The term "inert gas" as used herein is a broad term, and is to be given its ordinary and customary meaning to a person of ordinary skill in the art (and is not to be limited to a special or customized meaning), and includes without limitation a gas that is relatively impermeable to the membrane as described herein. In some embodiments, the inert gas comprises one or more of nitrogen, argon, helium, or other noble gases. In another embodiment, the inert gas is nitrogen. In another embodiment, the inert gas is dry nitrogen.

The term "source liquid" as used herein is a broad term, and is to be given its ordinary and customary meaning to a person of ordinary skill in the art (and is not to be limited to a special or customized meaning), and refers without limitation to a liquid solution that provides the source of a gas through change of phase used in an application or process, specifically a process gas.

The term "head space" as used herein is a broad term, and is to be given its ordinary and customary meaning to a person of ordinary skill in the art (and is not to be limited to a special or customized meaning), and refers without limitation to a volume of gas in fluid contact with a source liquid that provides at least a portion of the gas contained in the head space.

The term "vaporizer" as used herein is a broad term, and is to be given its ordinary and customary meaning to a person of ordinary skill in the art (and is not to be limited to a special or customized meaning), and refers without limitation to a device comprising a source liquid, a headspace, a heater, a carrier gas inlet, a carrier gas outlet, and a permeable or selectively permeable barrier separating the head space from the source liquid where the source liquid changes phase and may be used as a process gas. Preferentially, the vaporizer contains a source liquid, a headspace, a heater, a carrier gas inlet, a carrier gas outlet, and a permeable or selectively permeable barrier separating the head space from the source liquid where the source liquid changes phase and may be used as a process gas. The gas generated from the source liquid by energy supplied by a heat source is swept away by the carrier gas. In certain embodiments the carrier gas is saturated. In other embodiments the carrier gas is not saturated.

The term "power" as used herein is a broad term, and is to be given its ordinary and customary meaning to a person of ordinary skill in the art (and is not to be limited to a special or customized meaning), and refers without limitation to a rate of energy consumed per unit of time. When applied to heater power is commonly measured in watts.

The following description and examples illustrate many embodiments of the present invention in detail. Those of ordinary skill in the art will recognize that there are numerous variations and modifications of this invention that are encompassed by its scope. Accordingly, the description of the embodiments herein should not be deemed to limit the scope of the present invention. In addition, US20150068611 is incorporated fully herein by reference.

In many embodiments of the methods, systems, and devices disclosed herein, a substantially gas-impermeable membrane is used to separate the gas phase of the multi-component source liquid from the liquid. In some embodiments, the ion exchange membrane is a resin. In some embodiments, the ion exchange membrane is a fluorine-containing polymer such as a fluorinated ion-exchange membrane in acid form. The ion exchange membrane may be a perfluorinated ionomer comprising a copolymer of ethylene and a vinyl monomer containing an acid group or salts thereof. The salts may be any one of, for example sodium, pyridinium, ammonium, potassium, magnesium, iron, aluminum or calcium salts. Exemplary perfluorinated ionomers include, but are not limited to, perfluorosulfonic acid/tetrafluoroethylene copolymers ("PFSA-TFE copolymer") and perfluorocarboxylic acid/tetrafluoroethylene copolymer ("PFCA-TFE copolymer"). These membranes are commercially available under the trade names NAFION® (E.I. du Pont de Nemours & Company), FLEMION® (Asahi Glass Company, Ltd), and ACIPLEX® (Asahi Chemical Industry Company). 3M IONOMER (3M Company) could also be used. A PFSA-TFE copolymer contains a tetrafluoroethylene (TFE) "backbone," to which perfluorosulfonic acid (perfluoro(4-methyl-3,6-dioxa-7-octene-1-sulfonic acid)) groups are attached. There are between one and six perfluorosulfonic acid groups per six TFE backbone units. PFSA-TFE copolymers are normally classified by Equivalent weight, or by grams of polymer per mole of functional group. Often, the copolymer is between: 500 EW or less; and 2000 EW or more. In certain embodiments, the ion exchange membrane may contain either a single copolymer or combinations of copolymers.

In certain embodiments, a single peak molecular weight is used. In certain embodiments, bimodal or multimodal molecular weights are used. In certain embodiments, the molecular weight can be in any configuration, including but not limited to: block, tapered, random, linear, and others.

PFCA-TFE copolymers contain a tetrafluoroethylene (TFE) "backbone," to which the perfluorocarboxylic acid (perfluoro(4-methyl-3,6-dioxa-7-octene-1-carboxylic acid)) groups are attached. The acid groups can be converted to salt form by a pretreatment with a suitable base. The pretreatment methods are well known in the art, and can be performed with manufacturer recommendation. Depending on the nature of the liquid to be vaporized, pretreatment conditions can be adjusted to optimize the membrane. Examples of pretreatment conditions that can be adjusted include but are not limited to: selection of base; solvents; temperature; among others.

Hydrophilicity can be adjusted by cross-linking with a hydrophilic agent or by co-casting. In such embodiments where hydrophilicity is adjusted by cross-linking with a hydrophilic agent or by co-casting, the polymer already includes cross-linkable groups, or is functionalized to include cross-linkable groups. Other pretreatments without modifying surface chemistry can be employed. In another embodiment, the polymer can be impregnated with inorganic oxides. This impregnation can improve thermal stability by 5° C.-120° C. This can also increase water transport rate properties by 2%-40%.

Typically, the membrane suppresses the diffusion of gases and other contaminants, such as particles, aerosols, viruses, bacteria, and prions. The thickness of the membrane is often between 0.5 microns and 2000 microns. The leak rate is measured by monitoring the pressure in an isolated static system. An example of a leak rate is $10^{-9}$ cm$^3$/cm$^2$/s for nitrogen at standard temperature and pressure. Leak rates can be as high as $10^{-3}$ cm$^3$/cm$^2$/s at standard temperature and pressure or as low as $10^{-11}$ cm$^3$/cm$^2$/s for a specific gas.

In many embodiments of the methods, systems, and devices disclosed herein, of generating a gas from a source liquid, the source liquid is contacted to a first side of a substantially gas impermeable membrane and the gas generated is received on the second side of the substantially gas impermeable membrane. In certain embodiments, the first and second sides of the substantially gas impermeable membrane have a flat form, wherein the membrane is a sheet. In other embodiments, the membrane can also be in a tubular or cylindrical form, wherein one surface forms the inner portion of a tube, and the opposing surface forms the outer portion of the tube. The membrane can take any form, provided that a first surface and an opposing second surface sandwich a bulk of membrane material.

Certain properties of the membrane can be adjusted, depending on the process conditions, the nature of the gas being generated, and other factors. Such adjustable properties may include, but are not limited to, the physical form of the membrane, the configuration of the membrane, the fabrication method of the membrane, the presence or absence of a support layer of the membrane, and the presence or absence of an active layer of the membrane. When the membrane is thin, the membrane is typically provided mechanical support. Thicker membranes can be used without such support.

In certain embodiments, the surface area of the membrane can be selected depending on the volume of gas to be generated. In other embodiments, the membrane comprises a composite or mixture of polymers. This composite or mixture of polymers can comprise two or more layers. The layers can have the same or different properties as one another. A layer can provide support to filtration for example.

In many embodiments, the membranes are in fiber form, rather than in sheet form, due to the ability to provide greater exposed membrane surface area in a fixed volume when fibers are employed.

In certain embodiments, the vaporizer contains the membranes which are fixed in a module or other suitable apparatus. In embodiments in which the membranes are in fiber form, preferably the membranes are arranged in cylindrical arrays or bundles. In other embodiments, other configurations can be employed, such as square, triangular, irregular, or other configurations. The membrane module preferably includes a plurality of hollow membrane fibers each of which extend longitudinally between, and are mounted at each end to, a respective header. In other embodiments, other configurations are contemplated, such as looped fibers wherein both ends are secured in a single header, among other configurations. The fibers can be taut or slack, close or loosely packed formation, or spaced apart. The fibers preferably have a packing density of from 5% or less to about 95% or more, or any density in between those two values. The fibers may optionally be partitioned into a certain number of bundles in order to form a space or spaces therein between. Optionally, a single bundle of fibers may be employed.

In some embodiments, spacing in between the fibers is maintained to facilitate circulation of the source liquid. Optionally, a fiber bundle can be protected by a module support screen or a casing can provide support to a header or headers or clips or rings can be employed to bind the fiber bundle. Materials employed in the header and any supports or casing are selected such that these materials are able to tolerate elevated temperature and pressure conditions and will resist reacting with or contaminating any gas generated. In some certain embodiments, one or more membrane modules may be arranged into a cassette or battery, each cassette or battery being provided with a source liquid, pumps, valves, and instrumentation.

In some embodiments, a carrier gas is used to contact the gas phase of the multicomponent source liquid. The gas generated from the source liquid, typically a gas, permeates the membrane and is swept away by carrier gas. The carrier gas may be saturated, oversaturated, or undersaturated with the gas generated by the source liquid. The carrier gas may be comprised of one or more of clean dry air, nitrogen, hydrogen, oxygen, argon, and carbon dioxide.

In certain embodiments the vaporizer contains level sensors, commercially available from, for example, GEMS. Those of ordinary skill in the art will recognize the use of level sensors in the embodiments of the methods, systems, and devices disclosed herein. In these and other embodiments the vaporizer contains thermal sensors, commercially available from, for example, Omega Engineering. Those of ordinary skill in the art will recognize the use of thermal sensors in the embodiments of the methods, systems, and devices disclosed herein. The vaporizer may further contain oven temperature sensors, commercially available from, for example, Omega Engineering. Those of ordinary skill in the art will recognize the use of temperature sensors in the embodiments of the methods, systems, and devices disclosed herein. The vaporizer may further contain a drain valve, commercially available from, for example, Biochem Fluidics. Those of ordinary skill in the art will recognize the use of a drain valve in the embodiments of the methods, systems, and devices disclosed herein. In these and other embodiments the vaporizer contains a replenishment vessel, commercially available from, for example, Biochem Fluidics. Those of ordinary skill in the art will recognize the use of a replenishment vessel in the embodiments of the methods, systems, and devices disclosed herein.

In many embodiments, a process gas generated from a source liquid can be delivered at sub-atmospheric pressures. Delivery at sub-atmospheric pressures is desirable in many applications, such as atomic layer deposition. Sub-atmospheric pressures can be achieved with downstream vacuum pumps. In certain embodiments, the device comprises a primary pump on the permeate side, and a second pump connected to the source liquid side. In these embodiments, the vapor pressure differential or downstream pressure can be managed by adjusting the power input to the vaporizer, amount of carrier gas flow rate, carrier gas pressure, pressure drop between the liquid to the permeate side, or downstream venting.

Once choke flow is reached across the membrane or on the permeate side of the vaporizer, further lowering of pressure on the permeate side of the vaporizer no longer increases the permeation rate across the membrane. Only by increasing the vapor pressure of the source liquid by adding power through the heater to the vaporizer will increase permeation of the gas generated by the source liquid increase.

In some embodiments the power supplied to the vaporizer is through heating the outside of the vaporizer with electrical heaters connected to a power source. One skilled in the art could apply energy through other method, such as steam, transfer liquids, heating of the carrier gas, and other techniques.

In some embodiments of the methods, systems, and devices disclosed herein, the power applied is an instantaneous power. Methods of calculating instantaneous power used to generate a gas mass flow rate from a source liquid may be done, for example by taking samples of the instantaneous current and line voltage of a vaporizer heater, multiplying the current and voltage values together to give an instantaneous power measurement, and, running an average of the 1-second cycle time with the appropriate scale factor, which determines the average power delivered to the heater. This power value is correlated to the mass flow rate of gas generated from the source liquid.

In some configurations and selection of devices that are used to measure and calculate the power input, the configuration and selection is done in order to overcome certain obstacles to accurate measurements. There are several obstacles to obtaining an accurate measure of energy input, including the fact that industrial power is noisy and distorted, depending on what other machinery or usages are draining power at the time of measurement. High speed sampling occurs at 960 samples per second. In some embodiments of the method, one may control circuitry to a 1-second Pulse Width Modulation cycle to account for the Pulse Width Modulation of the power to the load. In this embodiment, the entire power cycle is measured, with no need to synchronize to the Pulse Width Modulation cycle.

In some embodiments, the Allegro ACS711 hall effect sensor is used to measure the current delivered to the load. The Allegro ACS711 has many benefits. It is smaller and more resistant to damage, and more immune to stray magnetic fields. It galvanically isolates the signal output side of the circuit from the line side of the circuit, produces a signal in the 3.3V range, dissipates almost no power, and is rated up to 12.5 amperes AC. Larger devices are available with ratings up to 50 AC, which may also be used if desired. The Allegro ACS711 also has a 100 Hz bandwidth in order to accurately measure large distortion.

A standard power transformer may be used in some embodiments. The power transformer preferably provides galvanic isolation, and scales the line voltage to an appropriate level for the circuitry to be measured. Preferably, there is a resistance divider on the secondary winding of the transformer, which causes consistent loading for the secondary winding, and a further reduction in scale. The transformer is rated at up to 220 VAC and 47-63 Hz, giving a worldwide performance possibility of 220 VAC or 208 VAC three-phase. The standard transformer has no bandwidth rating, but small transformers typically have bandwidths into the kilohertz range.

In many embodiments, the device contains a multi-channel analog-to-digital converter. The multi-channel analog-to-digital converter preferably samples the line voltage and the currents delivered to loads. In certain embodiments, the device preferably contains a circuit microprocessor. Preferably, measurements of the voltage and power are completed through firmware exercises.

In these and other embodiments, the appropriate scale factor is preferably applied to give the RMS AC voltage of the line.

Separate current measurements are not required on the current system. This would entail repeating the "square root of the sum of the squares" algorithm on sampled current waveforms. Multiplying the root mean square of the voltage times the root mean square of the current gives the mean power, not the average power. This does not account for the power factor or non-sinusoidal distortion, and cannot be used to provide an accurate measurement of the average power used. An averaging of instantaneous power provides an accurate measurement of the average power used.

Some embodiments of the methods of the methods, systems, and devices disclosed herein comprise determining at least one coefficient of a mathematical relationship between the mass flow rate of gas generated from the source liquid and the substantially instantaneous power used by the vaporizer heater. Different values of power are input to the heater while maintaining outlet pressure and carrier flow rate constant. The mass flow rate of gas generated from the source liquid for each power input is then measured. The process of measuring the mass flow of gas then repeated for different carrier gas flow rates and outlet pressures. A relationship is then determined between the mass flow rate of the gas and the power supplied to the heater such that at least one coefficient of a mathematical relationship exists and preferentially the relationship is that the coefficient is linear. The data collected is used to generate a linear equation that relates heater power to mass flow rate of the gas generated from the source liquid without including a variable for carrier gas flow rate, vaporizer source liquid temperature or outlet pressure. Thus, the mass flow rate of the generated gas is substantially independent of the flow rate of the carrier gas, the source liquid temperature, and the partial pressure of the carrier gas. This equation may also include a variable for saturation state of the carrier gas.

Using this equation, a target mass flow rate may be chosen and then input into the equation and a target heater power value is generated. The heater power value is then applied by the vaporizer heater and a mass flow rate of gas generated from the source liquid is created. The control system determines the instantaneous power use and compares it to the target power use. The controller corrects the value to match the measured power to the actual power by increasing or decreasing the instantaneous power applied to the heater. Power is increased or decreased by changing the amount of time current is allowed to flow into the heater during each heating cycle. The time the current is allowed to flow into the heater is controlled by solid state relays inside the controller.

In some embodiments, the mass flow rate generated is between 0.001 g per minute and about 100 g per minute, including between about 0.01 g per minute and about 10 g per minute, including between about 0.5 g per minute and about 5 g per minute. In these and other embodiments, the carrier gas flow rate is between about 0.001 slm and about 1000 slm, including about 0.1 slm and about 100 slm. In these and other embodiments, the carrier gas pressure is between about 0.0001 torr and about 1000 psig, including about 0.001 torr and about 100 psig, including about 1 torr and 15 psig, and including about 50 torr and 2 psig.

In some embodiments of the methods of the methods, systems, and devices disclosed herein, the vaporizer may be configured to control the substantially instantaneous power used by the heater based on the determined coefficient or coefficients of the mathematical relationship and, a target mass flow rate of the gas generated from the source liquid.

In other embodiments of the methods of the methods, systems, and devices disclosed herein, the vaporizer may be configured to control the target mass flow rate of gas generated from the source liquid based on the coefficient or coefficients and a target substantially instantaneous power usage by the heater.

The multicomponent source liquid typically comprises at least one of the following: hydrogen peroxide, hydrazine, an alcohol, water, amines, or mixtures comprised of hydrogen peroxide, hydrazine, alcohols, water, and amines. The multicomponent source liquid may comprise hydrogen peroxide and water where hydrogen peroxide is the less volatile component. In many embodiments of the methods, systems, and devices disclosed herein, the generated process gas is delivered to a critical process application.

In certain embodiments of the invention, water may be used as a surrogate source liquid for calibration in place to another liquid source. In order to conserve and minimize risk by using expensive or dangerous liquids as seldom as possible, it is desirable to use water as a surrogate liquid for more dangerous or expensive liquids when calibrating and/or testing a vaporizer. There are many variables to that differ between the intended process liquid and water for water to be accurately and easily used unless a simple relationship can be found between water and another liquid source. In order to facilitate this surrogate calibration and testing, one would need a control and calibration method independent of the flow rate of the carrier gas, independent of the temperature of the liquid, and independent of the pressure of the carrier gas.

The proposed method claimed herein is to control only the power input into the source liquid. The power required to vaporize liquid is generally much greater than the power required to raise the temperature of a liquid or a gas. The amount of vapor generated is directly and somewhat linearly related to the amount of power input into a system. This method allows for easier calibration, because instead of controlling and calibrating for the flow rate and pressure of the carrier gas and the temperature of the liquid, the only measurement that needs to be controlled is the amount of power input into the liquid. Because the values of heat of vaporization for most chemistry are already known, a surrogate chemical such as water may be used for the calibration of a system. Even very complicated blends of chemistries need only be compared with simple two-point calibration curves in order to determine the surrogate coefficient. This enhanced possibility of using safe and inexpensive chemicals as calibration surrogates improves productivity, safety, and conserves resources.

In these embodiments, the method comprises: determining at least one coefficient in a mathematical relationship between a mass flow rate for a gas generated from the first source liquid for a given substantially instantaneous power usage in a first vaporizer, determining at least one coefficient in a mathematical relationship between a mass flow rate for a gas generated from second source liquid for the same given substantially instantaneous power usage in the first vaporizer, determining a mathematical calibration relationship between the two previous mathematical relationships, determining at least one coefficient in a mathematical relationship between the mass flow rate for a gas generated from the first source liquid for a given substantially instantaneous power usage in a second vaporizer, and using this calibration relationship from the first vaporizer to modify the mathematical relationship determined by using the first source liquid in the second vaporizer to determine a mathematical relationship between a mass flow rate of the gas generated from the second source liquid for a given substantially instantaneous power usage in the second vaporizer.

In one preferred embodiment, the method comprises: determining at least one coefficient in a mathematical relationship between a water vapor mass flow rate from a liquid water source for a given substantially instantaneous power usage in a first vaporizer, determining at least one coefficient in a mathematical relationship between a mass flow rate for a gas generated from second source liquid for the same given substantially instantaneous power usage in the first vaporizer, determining a mathematical calibration relationship between the two previous mathematical relationships, determining at least one coefficient in a mathematical relationship between a water vapor mass flow rate from a liquid water source for a given substantially instantaneous power usage in a second vaporizer, and using this calibration relationship from the first vaporizer to modify the mathematical relationship determined by using water in the second vaporizer to determine a mathematical relationship between a mass flow rate of the gas generated from the second source liquid for a given substantially instantaneous power usage in the second vaporizer.

In these embodiments, the device comprises: determining at least one coefficient in a mathematical relationship between a mass flow rate for a gas generated from the first source liquid for a given substantially instantaneous power usage in a first vaporizer, determining at least one coefficient in a mathematical relationship between a mass flow rate for a gas generated from second source liquid for the same given substantially instantaneous power usage in the first vaporizer, determining a mathematical calibration relationship between the two previous mathematical relationships, determining at least one coefficient in a mathematical relationship between the mass flow rate for a gas generated from the first source liquid for a given substantially instantaneous power usage in a second vaporizer, using this calibration relationship from the first vaporizer to modify the mathematical relationship determined by using the first source liquid in the second vaporizer to determine a mathematical relationship between a mass flow rate of the gas generated from the second source liquid for a given substantially instantaneous power usage in the second vaporizer and delivering a mass flow rate of the gas generated from the second source liquid for a given substantially instantaneous power usage in the second vaporizer.

In one preferred embodiment, the device comprises: determining at least one coefficient in a mathematical relationship between a water vapor mass flow rate from a liquid water source for a given substantially instantaneous power usage in a first vaporizer, determining at least one coefficient in a mathematical relationship between a mass flow rate for a gas generated from second source liquid for the same given substantially instantaneous power usage in the first vaporizer, determining a mathematical calibration relationship between the two previous mathematical relationships, determining at least one coefficient in a mathematical relationship between a water vapor mass flow rate from a liquid water source for a given substantially instantaneous power usage in a second vaporizer, using this calibration relationship from the first vaporizer to modify the mathematical relationship determined by using water in the second vaporizer to determine a mathematical relationship between a mass flow rate of the gas generated from the second source liquid for a given substantially instantaneous power usage in the second vaporizer and delivering a mass flow rate of the gas generated from the second source liquid for a given substantially instantaneous power usage in the second vaporizer.

In one embodiment the given substantially instantaneous power usage is the same for both first and the second source liquid and the difference in mass flow rate is used in the calculation to determine the coefficient.

In another embodiment the several mass flow rates for the first and second source liquid are the same and the difference in instantaneous power usage is used in the calculation to determine at least one of the coefficients in a linear model.

Further, the first source liquid comprises at least one of the following: hydrogen peroxide, hydrazine, alcohols, water, amines, or mixtures comprised of hydrogen peroxide, hydrazine, alcohols, water, and amines. Preferably the first liquid source comprises water.

Further, the second source liquid comprises at least one of the following: hydrogen peroxide, hydrazine, alcohols, water, amines, or mixtures comprised of hydrogen peroxide, hydrazine, alcohols, water, and amines. Preferably the second source liquid comprises hydrogen peroxide and water.

In one embodiment of the invention, the vaporizer may be configured to control the substantially instantaneous power used by the heater based on: the determined coefficient or coefficients of the mathematical relationship; and, a target mass flow rate of the gas generated from the source liquid.

In one embodiment of the invention, the vaporizer may be configured to control the target mass flow rate of gas generated from the source liquid based on the coefficient or coefficients and a target substantially instantaneous power usage by the heater.

Figure 4:
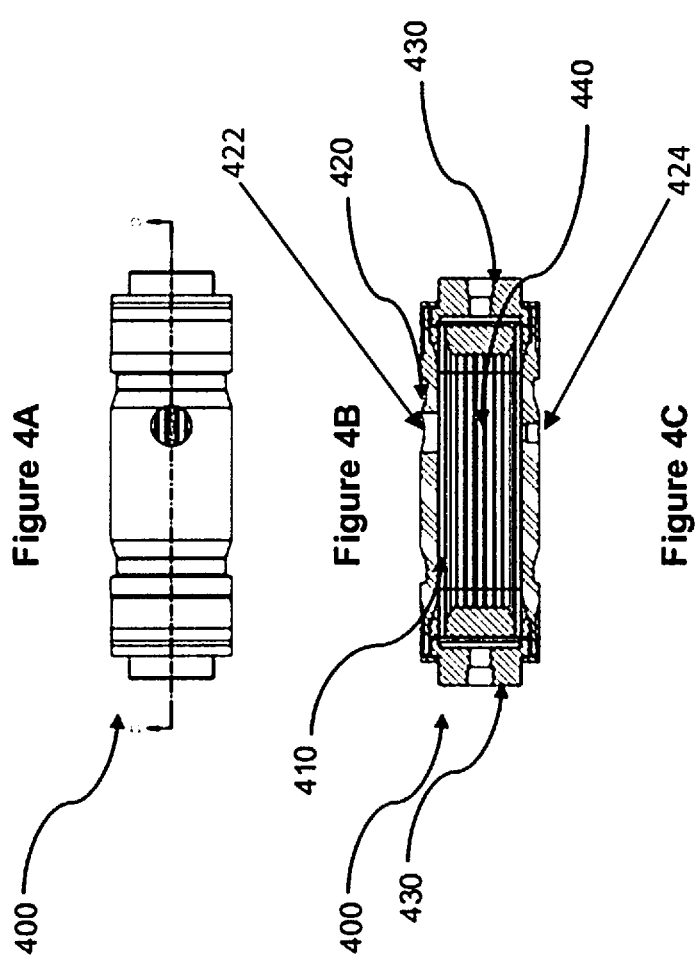
FIG. 4A is a front view of the membrane vaporizer assembly useful in certain embodiments of the present invention, such as an HPDA.
FIG. 4B is a cross sectional view of a membrane vaporizer assembly useful in certain embodiments of the present invention, such as an HPDA.
FIG. 4C is a front perspective view of a membrane vaporizer assembly useful in certain embodiments of the present invention, such as an HPDA.

FIGS. 4A, 4B, and 4C show a membrane vaporizer assembly 400, according to certain embodiments. Membrane vaporizer assembly 400 comprises a membrane assembly 410 within a shell housing 420 and end caps 430 configured to couple to shell housing 420. Membrane assembly 410 comprises a plurality of membrane lumens 440. The membrane lumens can be constructed from a fluorinated sulfonic acid membrane, for example, NAFION® membrane.

A membrane vaporizer assembly 400 can be configured to operate as a hydrogen peroxide delivery assembly (HPDA). An HPDA can provide a container for a hydrogen peroxide containing solution with a head space separated from the hydrogen peroxide containing solution by a membrane, e.g., a substantially gas-impermeable membrane. The housing 420 includes branches 422 and 424 which are used to fill, empty or refill the membrane vaporizer. Additional ports can be added to monitor source liquid temperature, allow gas to escape and monitor source liquid level. In some embodiments, a thermal heater jacket can be wrapped around shell 420, and end caps 430. In other embodiments the heater jacket may be wrapped only the shell 420 and either of the end caps 430 or solely around the shell 420.

Vaporizer can mounted horizontally, or preferably vertical with gas flow from top to bottom. In other embodiments the gas flow can be down. The source liquid can be stagnant or recirculated within the vaporizer.

Figure 5:
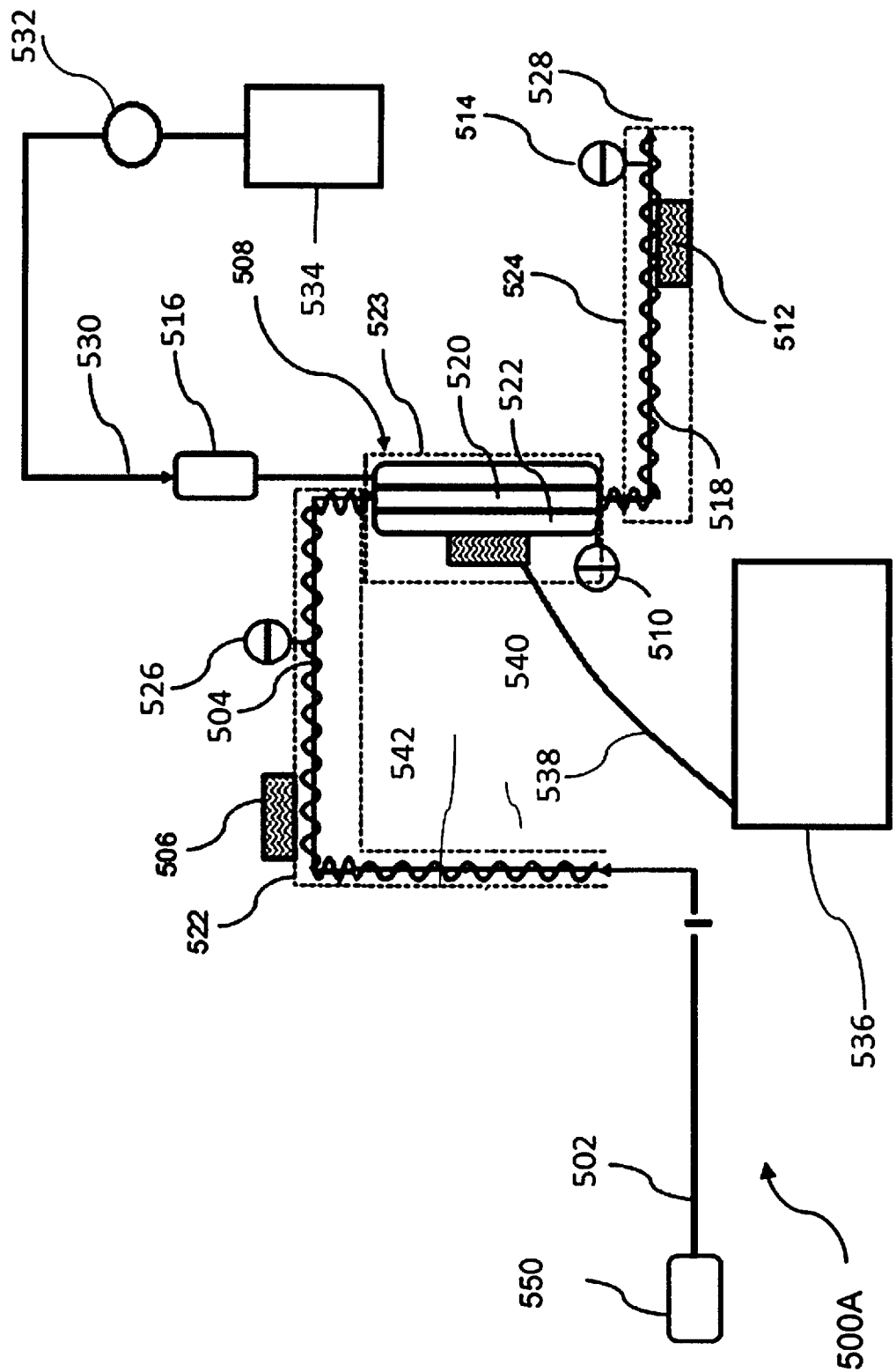
FIG. 5 is a P&ID of a delivery system according to certain embodiments of the present invention.

FIG. 5 shows a P&ID for a Peroxidizer delivery system 500A for delivering a gas generated from a source liquid. Delivery system 500A can comprise a carrier gas 550 in fluid communication with an HPDA 508, e.g., a membrane. In such configuration, delivery system 500A can be configured to receive a carrier gas 550 through a gas tubing 502.

In some embodiments the temperature of the carrier gas can be measured thermocouple 526 and can be maintained or changed by controller 536 by heating gas tube 504 with heater 522. The temperature can be controlled from ambient to 150° C. Preferably, the temperature can be controlled from 50° C. to 100° C.

Carrier gas can then flow into membrane vaporizer assembly 508, which can be an HPDA. Membrane vaporizer assembly 508 can comprise a plurality of membrane lumens 520 and a source liquid 522 (e.g., aqueous hydrogen peroxide solution) contained within the shell of membrane vaporizer assembly 508. Carrier gas can flow into membrane lumens 520 where source liquid 522 is volatized through membrane lumens 520. The concentration of gas from the source liquid entering the carrier gas can be controlled through power input from heater 540. The source liquid 522 is heated with a heater 540, and the temperature of the source liquid can be measured with thermocouple 510. The power input by heater 540 causes gas generated from source liquid 522 to vaporize across lumens 520 and be picked up by carrier gas 550 to form a process gas 542 comprised of a carrier gas 550 and gas generated from the source liquid 522. The process gas 542 can be saturated, undersaturated, or oversaturated. The concentration of gas from the source liquid in the gas phase can be increased or decreased to a setpoint by increasing or decreasing the power input to heater 540. The power to the heater jacket 540 is controlled by controller 536. Current and voltage in heater 540 are controlled and maintained by 536 through cable 538.

The process gas 542 exiting membrane vaporizer assembly 508 through gas tube 518 contains gas generated from the source liquid 522. The temperature of that process gas 542 can be controlled using a heater 512 and a thermocouple 514. Heater 512 can wrap around gas tube 518. The process gas 542, which contains the gas generated from the source liquid 522 can be delivered to a process throughout outlet 528. The temperature of tube 518 can be temperature controlled between ambient to 150° C. Preferably, tube 518 is heated to a temperature hot enough to prevent condensation of the process gas 542.

The calibration values are stored in controller 536, so that user input for mass flow rate of gas generated from the source liquid can be generated in 508, carried away by carrier gas 550 to process 528.

In certain embodiments the gas generated from the source liquid 522 has a mass flow rate. Preferably the mass flow rate of the gas generated from source liquid 522 is between 0.001 grams per minute and 100 grams per minute. More preferably the mass flow rate of the gas generated from source liquid 522 is between 0.01 grams per minute and 10 grams per minute. Most preferably the mass flow rate of the gas generated from source liquid 522 is between 0.5 grams per minute and 5 grams per minute.

The source liquid 522 contained in membrane vaporizer assembly 508 can be filled and replenished through fill tube 530. In some embodiments, this replenishment occurs so that the volume of source liquid 522 remains approximately constant. A replenishment tank 534 stores source liquid 544 which can be moved by pump 532 to maintain a relatively constant volume of source liquid 522 in vaporizer 508. The level of source liquid 522 in vaporizer 508 is maintained and controlled by controller 536 by activating when needed pump 532 and monitoring the liquid level in vaporizer 508 by a level sensor 516.

If the source liquid is a multicomponent mixture, then the source liquid in the replenishment vessel 544 may be the same or maybe different than the source liquid in the vaporizer 508. Preferably the source liquid in vaporizer 508 has a higher concentration of the less volatile component than in the source liquid in the replenishment vessel 544.

By the approach described herein, the molar ratio of hydrogen peroxide and water in the solution used for replenishing the aqueous hydrogen peroxide source can be the same as the molar ratio of these constituents in the resulting gas phase. For example, flowing a carrier gas through a gas phase of an aqueous hydrogen peroxide source to remove the gas phase containing the hydrogen peroxide can preferentially remove water, and reduce the initial volume of the aqueous hydrogen peroxide source. Using a substantially dry carrier gas accelerates removal of water from the aqueous hydrogen peroxide source. The hydrogen peroxide concentration in the remaining volume of the aqueous hydrogen peroxide source will increase as a consequence. Replenishing the partially depleted aqueous hydrogen peroxide source by adding an aqueous hydrogen peroxide solution, for example to maintain an essentially constant volume, provides a way to stabilize the molar ratio of hydrogen peroxide and water in the resulting combined gas phase (i.e., the gas mixture resulting from the carrier continuously sweeping away the gas phase generated by the aqueous hydrogen peroxide source). Importantly, the maintained constant volume can be the initial volume of the aqueous hydrogen peroxide source, or a lesser volume. Thus, hydrogen peroxide gas generated as a result of the carrier gas contacting the aqueous hydrogen peroxide source can be delivered in a stable steady-state concentration when the aqueous hydrogen peroxide source is maintained at a constant volume by addition of an aqueous hydrogen peroxide solution having a hydrogen peroxide concentration lower than the aqueous hydrogen peroxide source at the time the replenishing solution is added.

Generally speaking, by adjusting power, the steady-state concentration of $H_2O_2$ delivered by the disclosed apparatus and method easily can be adjusted. When electrical current is supplied by the control unit 536 through wires 538 to heater 540, power is generated by the heater to convert source liquid 522 to gas 542 across membrane 520. The instantaneous voltage and current measured in controller 536 calculates the instantaneous power being used. This is compared to user defined setpoint in grams/minute or ppm combined with the carrier gas flow rate. That value is raised or lowered based on the calculation equation with at least one coefficient of a mathematical relationship between power input from the heater and mass of the source liquid evaporated. In some embodiments the relationship between the mass flow rate of evaporated gas generated from the source liquid and power input is linear. This equation will be generally true for a range of mass flow rates, carrier gas flow rates and process delivery pressures.

Carrier gas is saturated, undersaturated, or oversaturated without affect to accuracy as the power is related to mass flow rate of the gas generated from the source liquid and swept away by the carrier gas. This eliminates the need to assume complete saturation of the carrier gas and exact vapor pressure of the source liquid.

In certain embodiments source liquid 522 is comprised of hydrogen peroxide, water, hydrazine alcohols, and amines. In other embodiments source liquid 522 is comprised of hydrogen peroxide and water. In other embodiments source liquid 522 is comprised of hydrazine. In other embodiments source liquid 522 is comprised of hydrazine and a nonpolar solvent. In other embodiments source liquid 522 is comprised of hydrogen peroxide and a nonpolar solvent.

In certain embodiments carrier gas 550 is comprised of air clean dry air, nitrogen, hydrogen, oxygen, argon, and carbon dioxide.

Example 1

Peroxidizer Mass Flow Rate Output Versus Power

Figure 3:
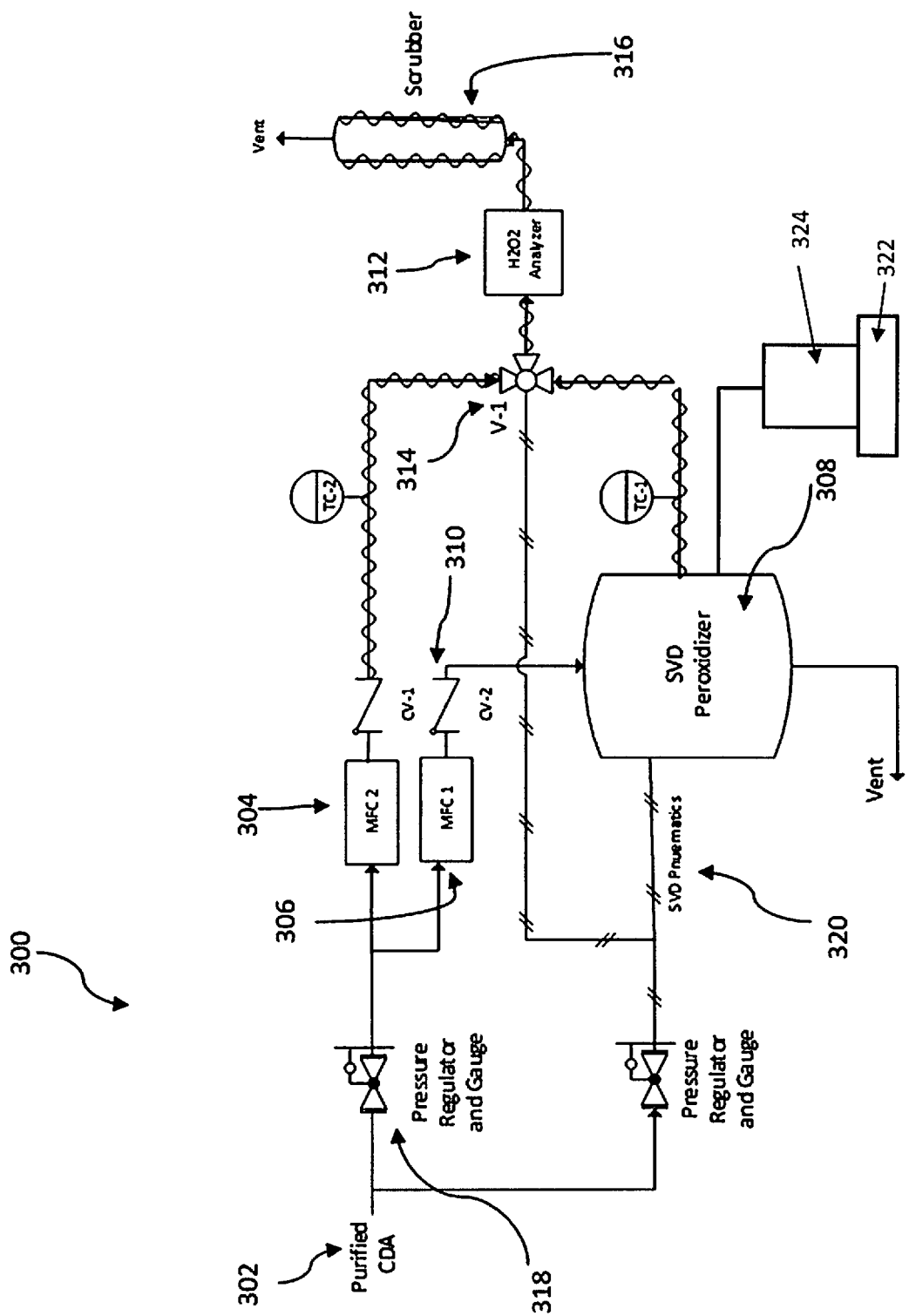
FIG. 3 is a P&ID of the experimental setup used to test Peroxidizer output versus power input

The apparatus of FIG. 3 was constructed to measure Peroxidizer 308 mass flow rate vapor output versus power input to the vaporizer heater. Clean dry air 302 was maintained at 25 psig with a forward pressure regulator 318 upstream of the mass flow controllers and 65 psig for the pneumatic valves 320. Two Brooks SLA5850S1EAB1B2A1 Mass Flow Controllers 304 and 306 were used to set the carrier gas mass flow rates for the Zero Gas (maximum 10 slm) and the Peroxidizer (maximum 50 slm). A check valve 310 was placed between the mass flow controller 306 and the Peroxidizer 308 to protect it from possible $H_2O$ and $H_2O_2$ exposure. Clean dry air 302 gas was run through the Peroxidizer 308 to add hydrogen peroxide and water vapor to the gas stream. A 30% cleanroom grade hydrogen peroxide was the source liquid for the Peroxidizer 308. Either the $H_2O_2$ vapor from the Peroxidizer or the clean dry air zero gas was delivered to the analyzer 312 with the PFA three-way pneumatic valve 314. The analyzers were heated to 120° C. to prevent condensation. The Peroxidizer's 308 hydrogen peroxide replenishment vessel 324 was weighed with a scale (Tree HRB3001) 322 to determine the solution consumption rate. The scrubber 316 was placed downstream of the analyzer 312 to convert the hydrogen peroxide into water and oxygen. The manifold tubing upstream of the analyzer was PFA. The heat-traced gas lines and components were controlled with an in-house temperature control box with Watlow 1/16 DIN controllers and kept at temperatures to prevent condensation. The entire manifold was setup inside of a fume hood. The Peroxidizer cover was installed during all test runs. An inline exhaust fan attached to the Peroxidizer's cabinet exhaust vent kept the internal cabinet pressure at negative 0.13 inches of water. The system was set to fill as soon as the liquid level was below the fill sensor. The pump was automatically set to pulse every 30 seconds if the a low level signal was not detected.

Figure 7A:
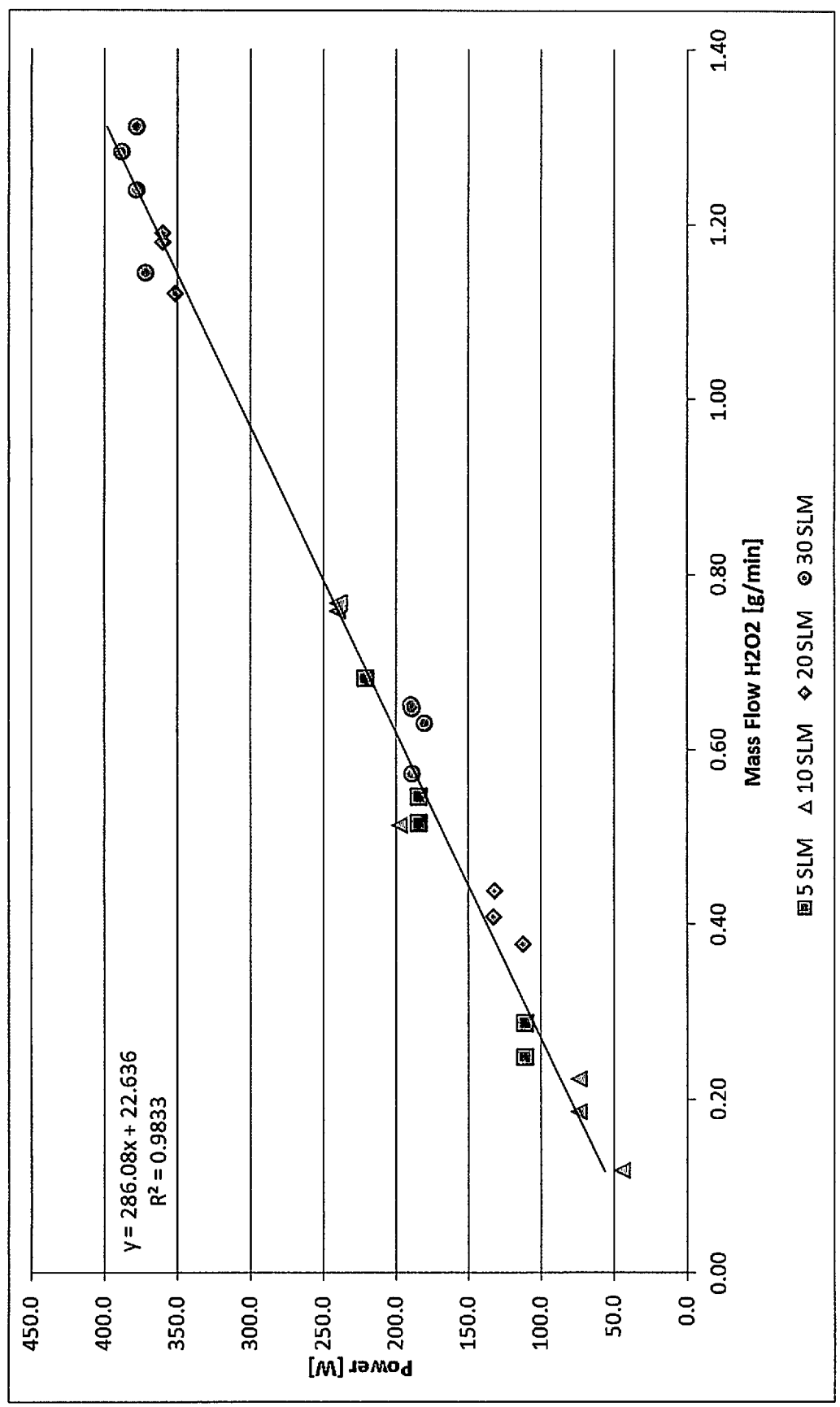
FIG. 7A is a graph showing that the mass flow of $H_2O_2$ is linear with respect to power for different flow rates.

FIG. 7A shows a linear relationship between the heater jacket power and the $H_2O_2$ mass flow rate for the test runs with Peroxidizer 308 during the power control testing. This linearity is independent of carrier gas flow. Previous tests on the Peroxidizer 308 showed a non-linear relationship between vaporizer source liquid temperature and the mass flow rate. Also, the vaporizer source liquid temperature for a given mass flow rate varied with the carrier gas flow rate. These results indicated that the calibration and control process can be minimized since multiple carrier gas rates are not required during calibration. For this system and the data collected, the following equation that would give the heater jacket power required to generate a mass flow rate of gas generated from a source liquid in a vaporizer.

$$\text{Power} = 286.08M + 22.636 \qquad \text{Equation (1)}$$

Where power is in watts, and M is the Mass flow rate of $H_2O_2$ in grams per minute.

The equation was generated over four different carrier gas flow rates, 5 slm, 10 slm, 20 slm, and 30 slm.

The data was fit to a first order linear equation shown above as $$y = 286.08X + 22.636. \qquad \text{Equation (2)}$$

The r squared linear regression coefficient was 0.983 which implies a highly linear relationship between mass flow rate of the gas generated from the source liquid and the power applied at the heater without significant dependence on the carrier gas flow rate.

Figure 7B:
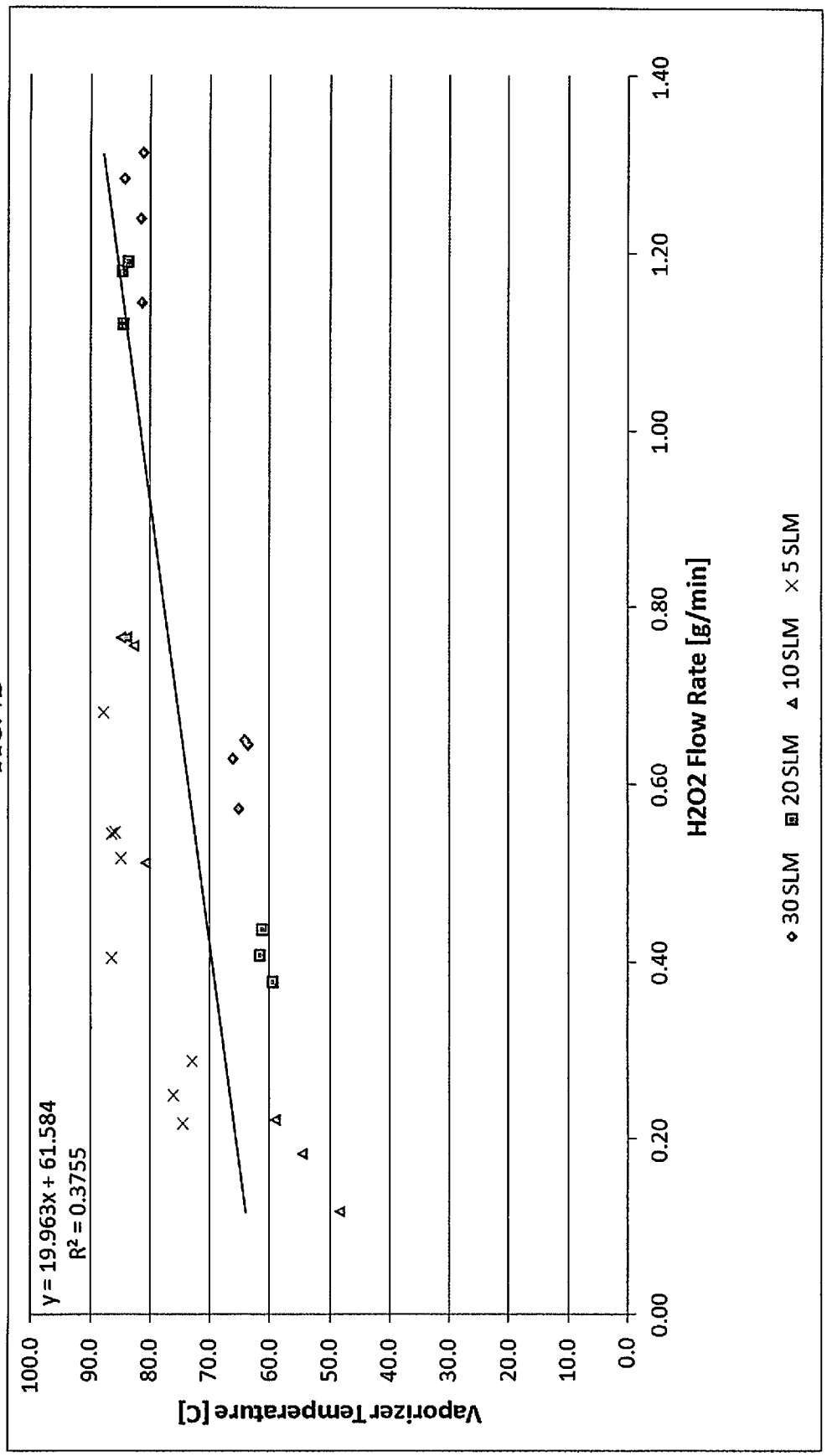
FIG. 7B is a graph showing that the mass flow of $H_2O_2$ is not linear with respect to vaporizer temperature

In FIG. 7B, the vaporizer temperature is plotted for different mass flow rates of $H_2O_2$ gas generated from the source liquid. When plotting data with different carrier gas flow rates, samples tended to lump together and were not linear. The linear equation for the graph was $$y = 19.96 * x + 61.584 \qquad \text{Equation (3)}$$

The r squared linear regression coefficient was 0.3755 which does not correlate with a linear relationship between vaporizer source temperature and mass flow rate generated from the source liquid. The output value is strongly influenced by the carrier gas flow rate and the power equation (2) does not demonstrate a correlation between carrier gas flow rate and mass flow rate of gas generated from the source liquid.

Data in concentration can be converted to mass flow rate in grams per minute as set forth in equation (4).

$$\text{Power} = 286.08 * \left( \left( \frac{\frac{\text{Flow Rate}}{22.4}}{\left( \frac{1E6}{\text{Concentration}} \right) - 5.2} \right) * 34 \right) + 22.636 \qquad \text{Equation (4)}$$

Where power is in watts, flow rate is in SLM, and concentration is in PPM.

Example 2

Water as a Surrogate

Testing was conducted to determine if water ($H_2O$) could be used as a surrogate gas for hydrogen peroxide gas generated from a source liquid for use in Rasirc's Peroxidizer calibration procedure. An experiment was run to prove if a correlation existed between hydrogen peroxide gas mass flow rate and water vapor mass flow rate.

The Peroxidizer delivers $H_2O_2$ gas for a range of concentrations with a 4.15:1 molar ratio of water to hydrogen peroxide from a 30% $H_2O_2$ replenishment source liquid. Initially, the Peroxidizer's $H_2O_2$ gas generation output was controlled by the vaporizer solution temperature. Experimentation had shown that the vapor output is not always repeatable using the solution temperature as a controlling point due among other things to a variation of the Thermocouple (TC) position, carrier gas flow rate, and carrier gas delivery pressure. In this set of tests, the vaporizer heater jacket power was the control point for the generated gas output. Past experimental data had shown that controlling mass flow rate output with heater power had provided improved stability and repeatability of mass flow rate when generated from the source liquid. The data also indicated a linear relation between the power and the mass flow rate of the $H_2O_2$ gas.

Figure 6:
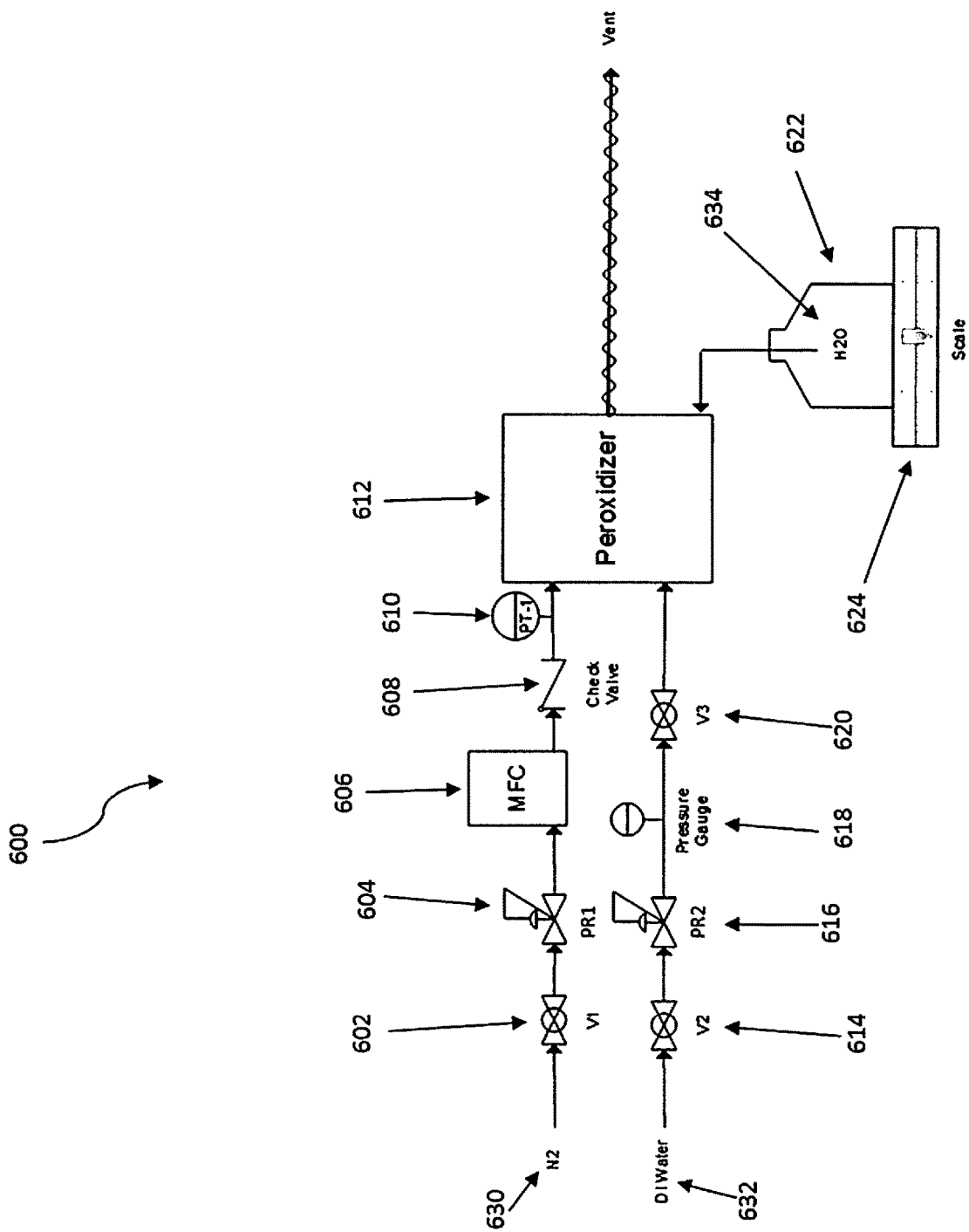
FIG. 6 is a P&ID of a test apparatus used in Example 2.

For this experiment, water was used as a source liquid to run Rasirc's Peroxidizer 612 instead of 30% hydrogen peroxide source liquid. The apparatus of FIG. 6 was constructed to test water vapor as a surrogate for $H_2O_2$ gas generated from a source liquid. Nitrogen gas 630 was used as a carrier gas. Deionized water 632 was connected to flush hydrogen peroxide from inside the Peroxidizer 612. Valve 602 was used to turn on and off the flow of nitrogen carrier gas. Pressure regulating valve 604 was used to set the upstream pressure of mass flow controller 606. Mass flow controller 606 was used to control the flow of nitrogen carrier gas. Check valve 608 was used to prevent backflow of hydrogen peroxide and water vapor. Pressure transducer 610 was used to read the pressure upstream of Peroxidizer 612. Valve 614 was used to turn on and off the flow of deionized water 632. Pressure regulating valve 616 and pressure gauge 618 were used to set the deionized water pressure upstream of the Peroxidizer 612.

The Peroxidizer 612 was tested with de-ionized water for different output setpoints and different carrier gas flow rates. Table 1 illustrates the tests parameters. The source reservoir 622 was filled with deionized water 634 and placed on an electronic scale 624 at the beginning of each test. An electronic scale (A&D Company FX-3000i) 624 was used to measure the mass of water consumed by the Peroxidizer 612 during each run. After all temperatures were stabilized, the water mass consumption was used to calculate the mass delivery and concentration of $H_2O$ vapor output by conservation of mass.

TABLE 1

| Run | Peroxidizer Setpoint (ppm) | Carrier Gas Flowrate (slm) |
|---|---|---|
| 1 | 30000 | 20 |
| 2 | 45000 | 10 |
| 3 | 50000 | 5 |
| 4 | 12500 | 20 |
| 5 | 12500 | 10 |

Table 2 displays the test data collected. The Peroxidizer's water vapor mass flow rate was controlled with the vaporizer's heater jacket power. The concentration of water vapor output was calculated using the scale measurement for the mass of water consumed during each run after all the temperatures in the system were reached and stabilized. The last column in Table 2 shows the mass flow of the water vapor output for the corresponding Peroxidizer target setpoint.

TABLE 2

| Run# | Peroxidizer Setpoint(ppm) | N2-Flow Rate (slm) | Water Vapor Output-Concentration (ppm) | Vaporizer Temperature (° C.) | Peroxidizer Pressure (torr) | Vaporizer Heater Jacket- Power (watt) | Water Vapor Mass Flow (g/min) |
|---|---|---|---|---|---|---|---|
| 1 | 30000 | 5 | 198286 | 58.6 | 777.2 | 66.5 | 1.006 |
| 2 | 30000 | 10 | 169168 | 60.7 | 785.6 | 77.4 | 1.647 |
| 3 | 30000 | 20 | 172202 | 69.8 | 811.2 | 103.7 | 3.357 |
| 4 | 30000 | 20 | 173646 | 70.6 | 805.9 | 104.9 | 3.380 |
| 5 | 45000 | 10 | 260247 | 72.7 | 786.7 | 101.0 | 2.846 |
| 6 | 50000 | 5 | 298683 | 68.4 | 778.4 | 84.4 | 1.714 |
| 7 | 12500 | 20 | 81279 | 50.9 | 802.4 | 64.6 | 1.458 |
| 8 | 12500 | 10 | 90684 | 48.7 | 786.2 | 55.1 | 0.846 |
| 9 | 30000 | 20 | 176359 | 69.1 | 811.9 | 103.7 | 3.444 |
| 10 | 45000 | 10 | 259044 | 70.0 | 794.1 | 98.2 | 2.813 |
| 11 | 12500 | 20 | 92734 | 50.5 | 803.3 | 64.5 | 1.644 |

Figure 8A:
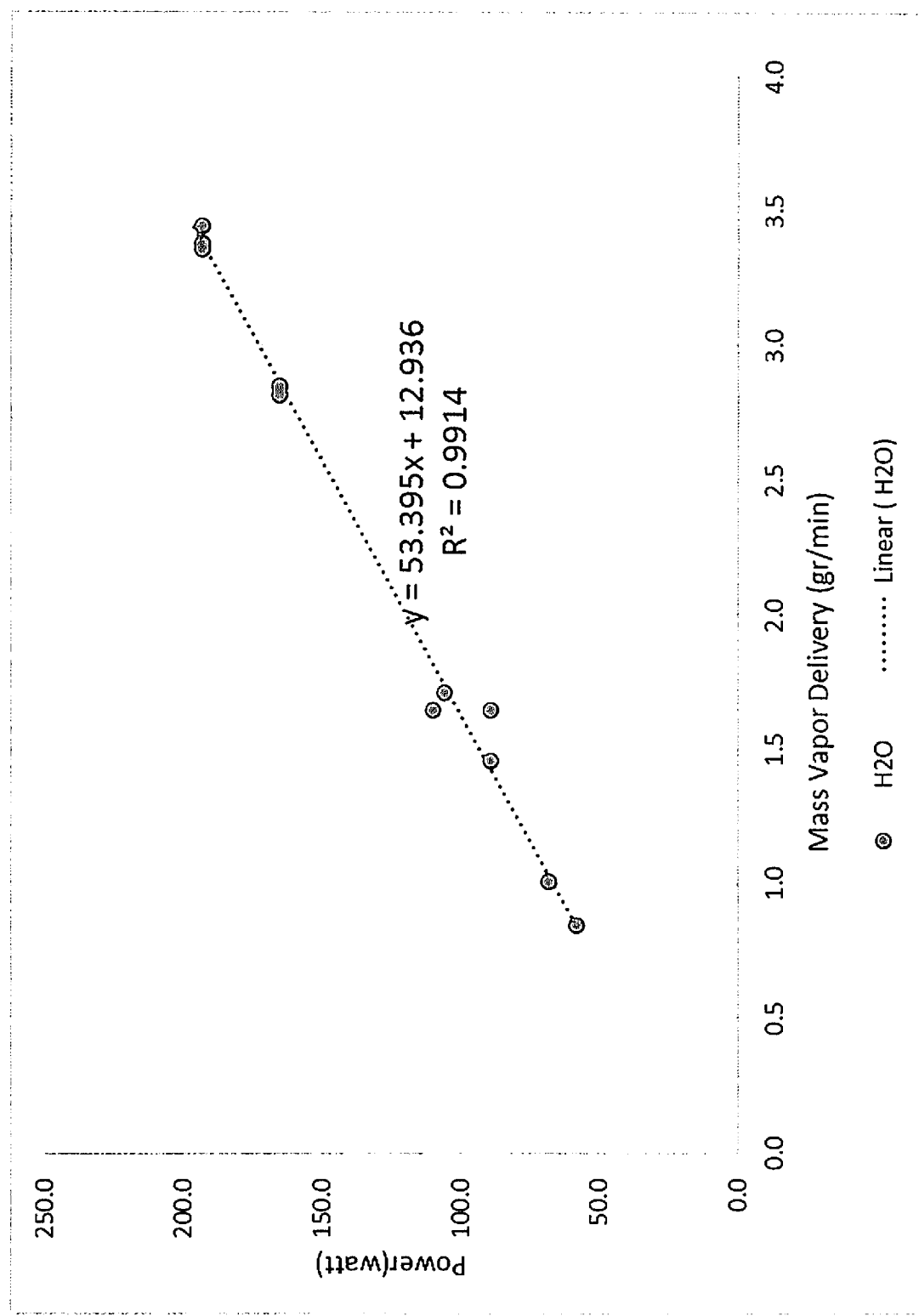
FIG. 8A is a graph showing linear relationships between mass flow rate of gas generated versus heater jacket power for $H_2O$ for both multiple carrier gas flows and water vapor mass flow rates.

FIG. 8A shows the mass flow of water vapor output versus the vaporizer heater jacket power. As shown, the relationship between the water vapor mass flow and the power was linear with water. The linear regression coefficient of R Squared was 0.99, which validated the assumption of a highly linear correlation between power applied to the vaporizer heater jacket and the mass flow rate of water vapor generated from the water source liquid. Values are for both multiple carrier gas flows and water vapor mass flow rates.

The Peroxidizer 612 was then run with 30% hydrogen peroxide replenishment source liquid. Carrier gas flow rates and power inputs were varied. Values are given in Table 3 below. The $H_2O_2$ gas mass flow rate generated from the source liquid is tabulated in column labeled $H_2O_2$ Delivery (g/min). In the next column, total gas mass flow rate generated from the source liquid which includes the total mass flow rate $H_2O_2$ gas and the water vapor generated from the $H_2O_2$ source liquid per unit time.

TABLE 3

| Run | Setpoint | Flow | Cal-Power | $H_2O_2$ Delivery (g/min) | Total Vapor Delivery(g/min) |
|---|---|---|---|---|---|
| 1 | 30000 | 20 | 193.5 | 1.04 | 3.35 |
| 2 | 45000 | 10 | 165.71 | 0.80 | 2.57 |
| 3 | 50000 | 5 | 105.75 | 0.38 | 1.21 |
| 4 | 12500 | 20 | 89.175 | 0.40 | 1.30 |
| 5 | 12500 | 10 | 57.651 | 0.19 | 0.60 |
| 6 | 45000 | 10 | 57.732 | 0.18 | 0.57 |

Figure 8B:
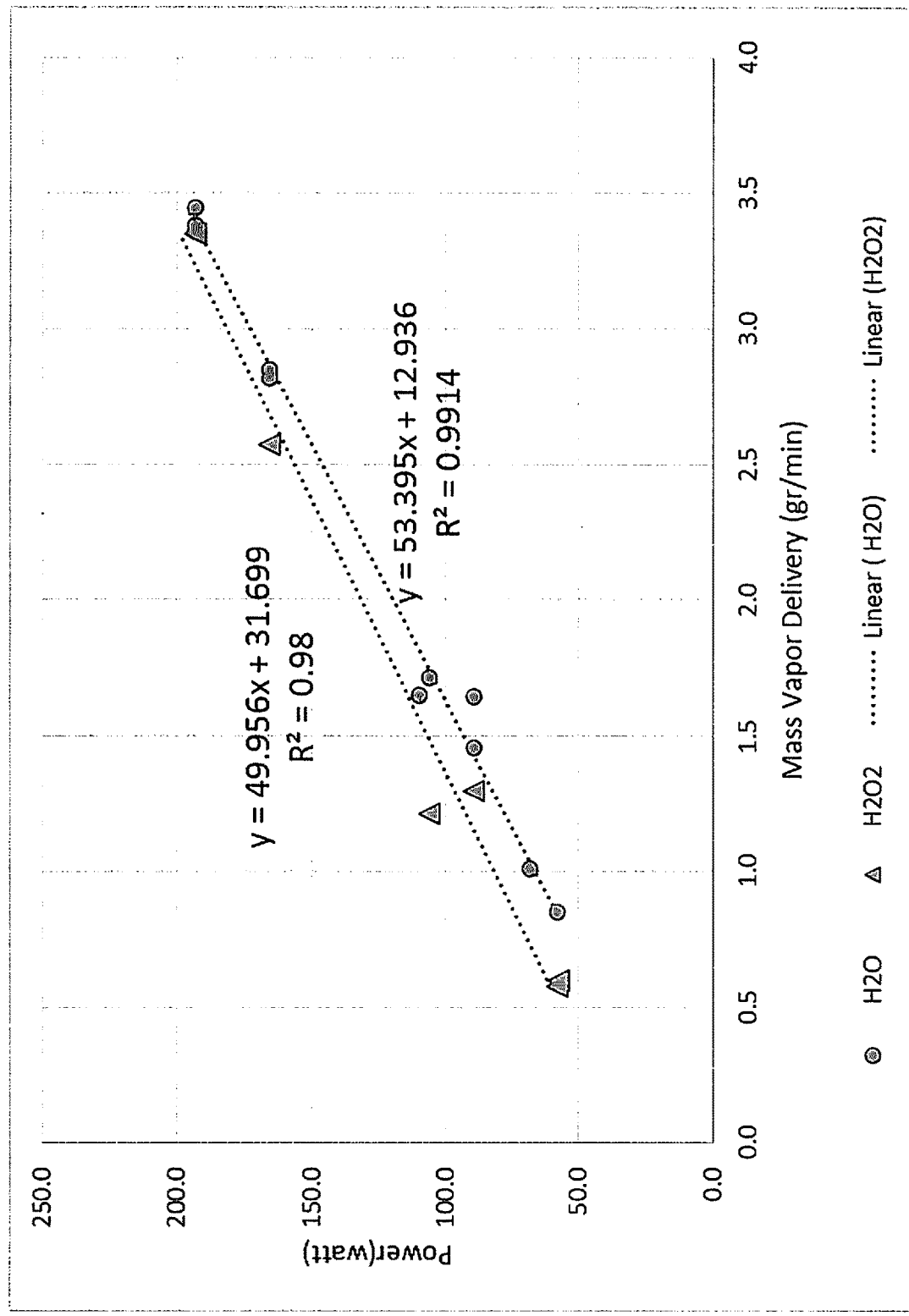
FIG. 8B is a graph showing linear relationships between mass flow rate of gas generated versus heater jacket power for $H_2O$ and $H_2O_2$.

In FIG. 8B, data for both water vapor (Table 2) and H2O2 gas (Table 3) were plotted. Both water vapor and $H_2O_2$ gas data plot as a liner relationship between mass flow rate of gas generated versus heater jacket power. Both demonstrated relative independence of carrier gas flow rate. Since both hydrogen peroxide and water mass flow rates are favorably linear with respect to the vaporizer heater jacket power, water can be used as a surrogate hydrogen peroxide liquid source for the Peroxidizer.

The mathematical relationship recorded in FIG. 8B for both water and hydrogen peroxide are very similar. The relationship for water vapor is Y=53.4*X+13. The relationship for H2O2 vapor is Y=50*X+31.7. One method to calibrate the Peroxidizer using water in place of H2O2 vapor is to run the system with water and collect at least two points to generate a new equation for heater jacket power versus water vapor mass flow rate, Y=M*X+B. To calibrate for H2O2 vapor, the equations from FIG. 8B are used to create correction factor.

This creates a new calibration equation, Y=(50/53.4)*M*X+(31.7−13)+B. In some cases the y intercept term B can be ignored. In other instances other factors can be added to take into account secondary effects such as room temperature, incoming gas temperature, heater jacket efficiency, cabinet exhaust and source liquid temperature.

Example 3

Stable Output Under Vacuum Conditions and Pressure Independence

The apparatus of FIG. 1 was constructed to determine if the Peroxidizer's power equation provides stable output under vacuum conditions and to determine if the power equation is pressure independent. The nitrogen and oxygen gas pressure was maintained at 25 psig with pressure regulators 102, 104, and 106. Mass flow controllers 110, 112 and 114 controlled the flow of the furnace's purge gas, the carrier gas for Peroxidizer 116, and the zero gas for the analyzer 118 respectively. Check valves 120, 122, and 124 were placed downstream of the mass flow controllers to prevent backflow of hydrogen peroxide and water vapor. The Peroxidizer 116 was used to deliver moisture and hydrogen peroxide vapor. Valve 126 was used to send the purge gas to process or to vent. Valve 128 was used to send the Peroxidizer's gas stream to process or to the analyzer. Valve 130 was used to send the zero gas to the analyzer 118 or to vent. Needle valve 132 and needle valve 134 were open throughout these tests. Thermocouple 136 and thermocouple 138 were placed in the gas stream to measure the gas temperature. The quartz furnace 140 maintained the temperature of the wafers during the oxidation process. A thermocouple 142 was inserted to measure the furnace temperature and it was removed prior to oxidation testing in order to not decompose the $H_2O_2$. Pressure transducer 144 monitored the gas pressure for the purge gas, and pressure transducer 146 monitored the pressure in the quartz tube 148. Pressure release valve 150 was used to prevent the quartz tube 148 from being over pressurized. Valve 152 was used to open the furnace 140 to atmospheric pressure while maintaining the Peroxidizer 116 at vacuum pressure to avoid destabilization of the system. A check valve 154 was used to prevent external contamination from being pulled into the furnace 140 when switching valve 152 to vent. A scrubber 156 was placed downstream of the furnace 140 and the $H_2O_2$ analyzer 118 to convert the $H_2O_2$ into water and oxygen. A scale was placed under the $H_2O_2$ refill bottle to measure the consumption rate of $H_2O_2$ solution and calculate $H_2O_2$ concentration delivered. A condenser 158 condensed the steam downstream of the scrubber 156, and a dropout pot 160 collected the water. A diaphragm pump 162 with a needle valve 108 upstream was used to maintain the vacuum pressure in the quartz tube 148 and Peroxidizer 116. All tests were done under the fume hood in an application lab. A Koyo Programable Logic Controller was used to collect the temperature and pressure data. The power control equation for this system was the following:

Power Output [W]=(0.000296*Carrier Gas Flow Rate [SLM]+0.000917)*$H_2O_2$Set Point [PPM]     Equation (5)

Table 4 shows the test conditions examined for this report. During this experiment, a constant flow of gas was fed to the pump to prevent destabilization of the Peroxidizer. Therefore, when the furnace was open to atmosphere, the zero gas was used as the make-up gas. When the Peroxidizer's gas stream was shifted to process, the analyzer was bypassed.

TABLE 4

| H2O2 Set Point [PPM] | Peroxidizer Pressure [torr] | Carrier Gas Flow [slm] | Purge Gas Flow [slm] | Zero Gas Flow [slm] |
|---|---|---|---|---|
| 70000 | 600 | 5 | 5 | 5 |
| 80000 | 400 | 5 | 1 | 1 |

The results indicate that the Peroxidizer could be run under vacuum pressure and maintain stability. Table 5 compares the set point concentration of hydrogen peroxide ("SP") with the measured concentration ("Disp H2O2").

TABLE 5

| Flow [SLM] | SP [PPM] | Disp H2O2 [PPM] | Disp± [PPM] | Disp± [%] | Scale H2O2 [PPM] | Diff [Disp − SP] | Diff [disp − Scale] | Diff [%] |
|---|---|---|---|---|---|---|---|---|
| 30 | 12,500 | 12480 | 188 | 1.51 | 13,193 | −20 | −713 | −5.70 |
| 20 | 12,500 | 12490 | 136 | 1.09 | 12,528 | −10 | −38 | −0.30 |
| 10 | 12,500 | 12492 | 282 | 2.26 | 11,347 | −8 | 1145 | 9.16 |
| 20 | 12,500 | 12494 | 178 | 1.42 | 13,365 | −6 | −871 | −6.97 |
| 30 | 25,000 | 24960 | 531 | 2.13 | 25,049 | −40 | −89 | −0.36 |
| 5 | 30,000 | 29984 | 798 | 2.66 | 31,542 | −16 | −1558 | −5.19 |
| 20 | 34,000 | 33952 | 912 | 2.69 | 32,285 | −48 | 1667 | 4.90 |
| 20 | 34,000 | 33943 | 896 | 2.64 | 32,513 | −57 | 1430 | 4.21 |
| 10 | 40,000 | 39909 | 823 | 2.06 | 39,585 | −91 | 324 | 0.81 |
| 5 | 50,000 | 49941 | 1687 | 3.38 | 50,173 | −59 | −232 | −0.46 |
| 5 | 60,000 | 59952 | 1368 | 2.28 | 61,149 | −48 | −1197 | −2.00 |

Figure 2:
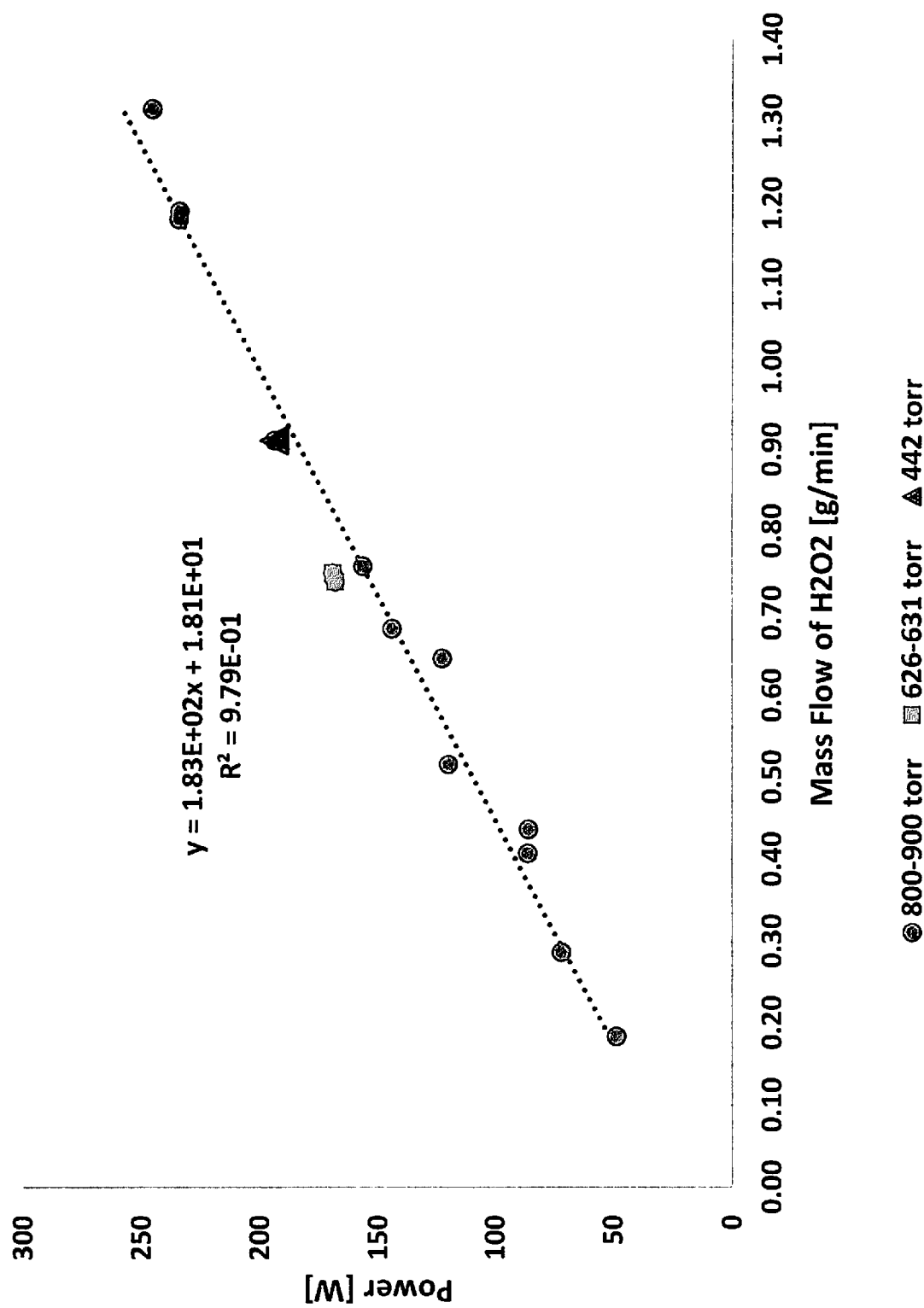
FIG. 2 is a graph showing that mass flow rate of $H_2O_2$ is linear with respect to power under different pressure conditions.

Peroxidizer data collected at 442 Torr and 626 and 631 Torr were plotted in FIG. 2. Additional data from Example 1 added to FIG. 2. All the data was fit to a linear equation and generated an R square correlation coefficient of 0.98. This high confidence R squared value demonstrated the mass flow rate of $H_2O_2$ gas generated from the source liquid has a linear relationship with power applied to the vaporizer heater. The relationship was relatively insensitive to the pressure of the carrier gas inside the vaporizer for the range from 442 to 800 Torr.

All references cited herein, including but not limited to published and unpublished applications, patents, and literature reference, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods, systems, and devices of the present invention. The disclosed methods, systems, and devices are susceptible to modification and alteration in their arrangement, manufacture, and use, which modifications and alterations will become apparent to those skilled in the art from a consideration of this disclosure. Consequently, it is not intended that the disclosed methods, systems, and devices be limited to the specific embodiments disclosed herein. Other embodiments of the invention will be apparent to those skilled in the art from consideration of the specification and practice of the invention disclosed herein.

The invention claimed is:

1. A method for controlling mass flow rate of a gas generated from a multi-component liquid source comprising: (a) providing in a vaporizer a multi-component liquid solution comprising a first component and a second component which is less volatile than the first component, wherein the vaporizer comprises a heater configured to receive an average power and heat the multi-component liquid solution; (b) providing the average power to the heater to generate a gas stream comprising the second component; (c) determining a first instantaneous power received by the heater by multiplying a first sampled instantaneous current and line voltage supplied to the heater and correlating the determined first instantaneous power to a first mass flow rate of the gas stream; (d) determining a second instantaneous power received by the heater by multiplying a second sampled instantaneous current and line voltage supplied to the heater and correlating the determined second instantaneous power to a second mass flow rate of the gas stream; (e) determining at least one coefficient of a mathematical relationship between mass flow rate of the gas stream and instantaneous power received by the heater based on the first and second instantaneous powers and the first and second mass flow rates; and (f) adjusting the average power provided to the heater to deliver a target mass flow rate of the gas stream based on the at least one coefficient, wherein the mass flow rate of the generated gas stream is independent of gas pressure in the vaporizer.

2. The method of claim 1, further comprising repeating steps (b)-(d) a plurality of times per second prior to performing step (e).

3. The method of claim 2, wherein steps (b)-(d) are repeated at least every 0.1 seconds.

4. The method of claim 1, wherein the multi-component liquid solution comprises hydrogen peroxide, water, hydrazine, alcohols, or amines.

5. The method of claim 4, wherein the multi-component liquid solution comprises hydrogen peroxide and water.

6. The method of claim 1, further comprising contacting the gas stream with a carrier gas flowing through the vaporizer to carry the gas stream to a critical process or application, wherein the mass flow rate of the gas stream is independent of a carrier gas flow rate through the vaporizer.

7. The method of claim 6, wherein the carrier gas is selected from the group consisting of nitrogen, hydrogen, argon, helium, steam, clean dry air, oxygen, $NH_3$, carbon dioxide and any combination thereof.

8. The method of claim 7, wherein the carrier gas is heated prior to contact with the gas stream.

9. The method of claim 1, wherein the target mass flow rate of the gas stream is between about 0.01 grams per minute and 50 grams per minute.

10. The method of claim 1, further comprising replenishing the multi-component liquid solution frequently to maintain a relatively stable volume of the multi-component liquid solution in the vaporizer.

11. The method of claim 1, further comprising contacting the multi-component liquid solution with a substantially gas-impermeable membrane within the vaporizer, wherein the substantially gas-impermeable membrane is configured to separate the multi-component liquid solution from the generated gas stream.

12. The method of claim 11, wherein the substantially gas-impermeable membrane is a fluorinated ion-exchange membrane.

13. A method for controlling mass flow rate of a gas generated from a multi-component liquid source comprising: (a) providing water in a vaporizer, wherein the vaporizer comprises a heater configured to receive an average-power and heat any liquid contained therein; (b) providing the average power to the heater to generate water vapor; (c) determining a first instantaneous power received by the heater by multiplying a first sampled instantaneous current and line voltage supplied to the heater and correlating the determined first instantaneous power to a first mass flow rate of the water vapor; (d) determining a second instantaneous power received by the heater by multiplying a second sampled instantaneous current and line voltage supplied to the heater and correlating the determined second instantaneous power to a second mass flow rate of the water vapor; (e) determining at least one first coefficient of a mathematical relationship between the first and second mass flow rate of the water vapor and instantaneous power received by the heater to generate a linear mathematical calibration relationship, wherein the at least one first coefficient of the mathematical relationship is determined based on the first and second instantaneous powers and the first and second mass flow rates; (f) after removing the water, providing in the vaporizer a multi-component liquid solution comprising a first component and a second component which is less volatile than the first component; (g) providing the determined first or second instantaneous power to the heater to generate a gas stream at a third mass flow rate, wherein the gas stream comprises the second component; (h) determining at least one second coefficient of a mathematical relationship between the third mass flow rate and the first or second instantaneous power received by the heater; and (i) adjusting the average power provided to the heater to deliver a target mass flow rate of the gas stream based on the at least one second coefficient, wherein the mass flow rate of the generated gas stream is substantially independent of gas pressure in the vaporizer.

14. The method of claim 13, wherein the multi-component liquid solution comprises hydrogen peroxide, water, hydrazine, alcohols, or amines.

15. The method of claim 14, wherein the multi-component liquid solution comprises hydrogen peroxide and water.

16. The method of claim 13, further comprising contacting the gas stream with a carrier gas flowing through the vaporizer to carry the gas stream to a critical process or application, wherein the mass flow rate of the gas stream is independent of a carrier gas flow rate through the vaporizer.

17. The method of claim 15, wherein the carrier gas is selected from the group consisting of nitrogen, hydrogen, argon, helium, steam, clean dry air, oxygen, $NH_3$, carbon dioxide and any combination thereof.

18. The method of claim 13, further comprising replenishing the multi-component liquid solution frequently to maintain a relatively stable volume of the multi-component liquid solution in the vaporizer.

19. A mass flow control system for controlling mass flow rate of a gas generated from a multi-component liquid source comprising:
(a) a multi-component liquid solution comprising a first component and a second component which is less volatile than the first component, wherein the multi-component liquid source provides a gas stream comprising the second component;
(b) a vaporizer configured to contain the multi-component liquid solution, wherein the vaporizer comprises a heater configured to receive an average power and heat the multi-component liquid solution; and
(c) a controller in electrical communication with the vaporizer and configured to:
(i) determine a first instantaneous power received by the heater by multiplying a first sampled instantaneous current and line voltage supplied to the heater and correlating the determined first instantaneous power to a first mass flow rate of the gas stream;
(ii) determine a second instantaneous power received by the heater by multiplying a second sampled instantaneous current and line voltage supplied to the heater and correlating the determined second instantaneous power to a second mass flow rate of the gas stream;
(iii) determine at least one coefficient of a mathematical relationship between mass flow rate of the gas stream and instantaneous power received by the heater based on the first and second instantaneous powers and the first and second mass flow rates; and
(iv) adjust the average power provided to the heater to deliver a target mass flow rate of the gas stream based on the at least one coefficient, wherein the mass flow rate of the generated gas stream is independent of gas pressure in the vaporizer.

20. The mass flow control system of claim 19, wherein the controller is further configured to repeat steps (i) and (ii) a plurality of times per second.

21. The mass flow control system of claim 20, wherein the controller is further configured to repeat steps (i) and (ii) at least 10 times per second.

22. The mass flow control system of claim 19, wherein the multi-component liquid solution comprises hydrogen peroxide, water, hydrazine, alcohols, or amines.

23. The mass flow control system of claim 22, wherein the multi-component liquid solution comprises hydrogen peroxide and water.

24. The mass flow control system of claim 19, further comprising a carrier gas flowing through the vaporizer and configured to carry the generated gas stream to a critical process or application, wherein the mass flow rate of the gas stream is independent of a carrier gas flow rate.

25. The mass flow control system of claim 24, wherein the carrier gas is selected from the group consisting of nitrogen, hydrogen, argon, helium, steam, clean dry air, oxygen, $NH_3$, carbon dioxide and any combination thereof.

26. The mass flow control system of claim 24, wherein the carrier gas is heated before entering the vaporizer.

27. The mass flow control system of claim 19, wherein the target mass flow rate of the gas stream is between about 0.01 grams per minute and 50 grams per minute.

28. The mass flow control system of claim 19, wherein the vaporizer is further configured to replenish the multi-component liquid solution frequently to maintain a relatively stable volume contained therein.

29. The mass flow control system of claim 19, wherein the vaporizer further comprises a substantially gas-impermeable membrane in contact with the multi-component liquid solution and the gas stream is provided by the second component penetrating the substantially gas-impermeable membrane.

30. The mass flow control system of claim 29, wherein the substantially gas-impermeable membrane is a fluorinated ion-exchange membrane.

31. The method of claim 1, wherein adjusting the average power provided to the heater further comprises changing an amount of time current flows into the heater during each heating cycle.

32. The method claim 13, wherein adjusting the average power provided to the heater further comprises changing an amount of time current flows into the heater during each heating cycle.

33. The mass flow control system of claim 19, wherein adjusting the average power provided to the heater further comprises changing an amount of time current flows into the heater during each heating cycle.

* * * * *

UNITED STATES PATENT AND TRADEMARK OFFICE
CERTIFICATE OF CORRECTION

PATENT NO. : 11,154,792 B2
APPLICATION NO. : 15/751044
DATED : October 26, 2021
INVENTOR(S) : Jeffrey J. Spiegelman et al.

It is certified that error appears in the above-identified patent and that said Letters Patent is hereby corrected as shown below:

In the Claims

Claim 13, Column 29, Line 2:
Please delete "substantially"

Claim 17, Column 29, Line 14:
Please delete "claim 15"
And insert --claim 16--

Signed and Sealed this
Twenty-second Day of February, 2022

Drew Hirshfeld
*Performing the Functions and Duties of the
Under Secretary of Commerce for Intellectual Property and
Director of the United States Patent and Trademark Office*